(12) United States Patent
Akatsuka et al.

(10) Patent No.: US 6,267,857 B1
(45) Date of Patent: Jul. 31, 2001

(54) OXYGEN SENSOR WITH A HEATER

(75) Inventors: Shoji Akatsuka, Bisai Aichi; Satoshi Ishikawa, Komaki Aichi, both of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/323,400

(22) Filed: Jun. 1, 1999

(30) Foreign Application Priority Data

Jun. 1, 1998 (JP) .................................................. 10-151481

(51) Int. Cl.$^7$ ................................................. G01N 27/407
(52) U.S. Cl. .......................... 204/424; 204/427; 204/428; 205/785
(58) Field of Search ........................... 204/408, 421–429; 205/785

(56) References Cited

U.S. PATENT DOCUMENTS

| | | | |
|---|---|---|---|
| 4,741,816 | * | 5/1988 | Nishio et al. ........................ 204/205 |
| 4,824,550 | | 4/1989 | Ker et al. . |
| 5,573,650 | | 11/1996 | Fukaya et al. . |
| 5,804,050 | | 9/1998 | Hayakawa et al. . |

FOREIGN PATENT DOCUMENTS

| | | |
|---|---|---|
| 2-054158 | 2/1990 | (JP) . |
| 4-157358 | 5/1992 | (JP) . |
| 9-325128 | 12/1997 | (JP) . |

* cited by examiner

Primary Examiner—T. Tung
(74) Attorney, Agent, or Firm—Morgan, Lewis & Bockius LLP

(57) ABSTRACT

The invention reduces the activation time of an oxygen sensor with a heater through rapid heating of an oxygen sensing element. A shaft-like heating member is inserted and fixed into an oxygen sensing element of a hollow shaft-like member while a terminal member intervenes therebetween. A heating portion is locally formed at an extreme end of the heating member. A surface of the heating portion is elastically pressed against an element inner wall, thereby establishing a laterally-abutting structure. A positioning projection is formed on an internal electrode connecting portion and projects toward the interior of the internal electrode connecting portion. The positioning projection is adapted to position the heating element within a hollow portion of the oxygen sensing element such that the axis thereof becomes substantially parallel to the axis of the hollow portion. Through employment of the laterally-abutting structure, heat generated in the heating portion is directly transferred to the oxygen sensing element. Also, heat radiated from a portion around the contact portion heats the oxygen sensing element in a supplementary manner. Therefore, the oxygen sensing element is heated swiftly to its activation temperature.

9 Claims, 21 Drawing Sheets

(a)

(b)

(a)

(b)

(a)

(b)

OXYGEN SENSOR WITH A HEATER

This application claims the benefit of Japanese Patent Application No. Hei. 10-151481, filed in Japan on Jun. 1, 1998, which is hereby incorporated by reference.

BACKGROUND OF THE INVENTION

1. Field of the Invention

The present invention relates to an oxygen sensor for sensing the oxygen concentration in exhaust gases from, for example, an internal combustion engine or to an oxygen sensor for sensing the oxygen concentration in a specific gas. More particularly, the present invention relates to an oxygen sensor with a heater which can quickly heat the oxygen sensor up to its required activation temperature.

2. Description of the Related Art

Recently, demand for purifying exhaust gases from an internal combustion engine of an automobile, for example, has been increasing. In these circumstances, an oxygen sensor with a heater has been developed which is able to accurately determine the oxygen concentration in the exhaust gases from the internal combustion engine even under a condition that the exhaust gas temperature is low, for example, at engine startup or while the engine is idling. Japanese Patent Application Laid-Open (kokai) No. 4-157358, for example, discloses an oxygen sensor which includes an oxygen sensing element of a hollow shaft-like member having a closed end and an electrode layer on the inner wall thereof, and a shaft-like heating member, which is disposed within the oxygen sensing element, for heating the oxygen sensing element. In the oxygen sensor, the shaft (bar)-like heating member (heater) is coaxially inserted into the inner space of the test-tube like oxygen sensing element, which is made of an oxygen-ion conductive solid electrolyte, until the extreme end thereof reaches or approaches the inner surface of the extreme end of the oxygen sensing element.

In the oxygen sensor described above, when the oxygen sensing element is heated in a nonuniform manner, sufficiently-heated and activated portions and insufficiently-heated and high-resistance portions coexist in the oxygen sensing element. The electrical resistance of the entire oxygen sensing element is frequently determined by the high-resistance portions. This results in prolonging the time until the resistance of the oxygen sensing element becomes satisfactorily low and is thus activated, viz., a rise time of the sensor. In the conventional sensor construction, the heating member is disposed coaxially with the oxygen sensing element, so that the oxygen sensing element is uniformly heated with respect to the circumferential direction and therefore uniformly activated with respect to the same direction. The extreme end of the heating member is in contact with or in proximity to the inner surface of the extreme end of the oxygen sensing element. Therefore, heat transfer from the extreme end of the heating member to the oxygen sensing element will be in a satisfactory level. In this respect, the goal of reducing the rise time of the sensor will be achieved to some extent.

However, conventional sensors have the following problems to be solved. When the bar-like heating member and/or the hollow oxygen sensing element is thermally expanded, the extreme end of the heating member may be spaced apart from the inner surface of the extreme end of the oxygen sensing element, thereby deteriorating heat transfer efficiency. Alternatively, the extreme end of the heating member may be pressed against the inner surface of the extreme end of the oxygen sensing element. In this case, a stress is generated, thus adversely reducing the durability of the device. Thus, the oxygen sensor is greatly influenced by the thermal expansion. This leads to nonuniformity of the heating state of the oxygen sensing element and a variation of the characteristics among individual oxygen sensor products. A possible approach to solve this problem is to form a relatively large space between the heating member and the oxygen sensing element. However, the approach fails to solve the problem because the heat transfer efficiency is lowered, and the sensor rise time is long.

Accordingly, when a reduction in the element rise time is desired, contact between the heating element and the oxygen sensing element becomes mandatory. In terms of a reduction in the sensor rise time, those skilled in the art consider it essential to dispose the oxygen sensing element and the heating element concentrically, for the purpose of attaining uniform heating of the oxygen sensing element So long as sensor design is bound by this concept, there is no alternative but to bring the extreme end of the heating element and the inner surface of the extreme end of the oxygen sensing element into contact. As a result, the conventional sensor construction, in which the extreme end of the heating member is in contact with or in proximity to the inner surface of the extreme end of the oxygen sensing element, involves a variation of characteristics among individual oxygen sensor products in return for a reduction in the sensor rise time. Therefore, the conventional sensor construction is not necessarily the best in terms of quick, effective heating of the oxygen sensing element.

SUMMARY OF THE INVENTION

An object of the present invention is to provide an oxygen sensor with a heater which can accurately sense the oxygen concentration in exhaust gases from an internal combustion engine, even under conditions where the exhaust gas temperature is low; for example, at engine startup or while the engine is idling, by quickly and efficiently heating an oxygen sensing element of a hollowed shaft-like member by a heating member contained in the sensing element, and which can suppress a variation of the characteristics of individual oxygen sensors to a minimum.

To achieve the object described above, an oxygen sensor with a heater (oxygen sensor) according to an embodiment of the invention includes: an oxygen sensing element having a hollow shaft-like member, which is closed at the extreme end and has electrode layers on the inner and outer sides thereof; a shaft-like heating member disposed within a hollow portion of the oxygen sensing element and adapted to heat the oxygen sensing element; and a fixture member comprising a fixture portion circumferentially surrounding the heating member and directly or indirectly (i.e., via another member) maintaining contact with the inner wall of the oxygen sensing element, and a heating-member holding portion being coupled with the fixture portion while being located at least at one side of the fixture portion as viewed in the axial direction of the heating member and being adapted to hold the heating member, thereby fixing the heating member within the oxygen sensing element by means of the fixture portion. A positioning projection is formed on at least either the fixture portion or the heating-member holding portion in such a manner as to project inward and abut the peripheral surface of the heating member. Through employment of such an abutting feature, the heating member is positioned such that the center line of the heating member is disposed eccentric (offset) to the center line of the hollow portion of the oxygen sensing element in the vicinity of a heating portion of the heating member. Preferably, as the result of such an eccentricity (offset), the surface of the heating portion of the heating member abuts the inner wall of the hollow portion of the oxygen sensing element. In other words, as a result of the fact that the center line of the heating member is eccentric (offset) to the center line of the hollow portion of the oxygen sensing element in the vicinity of the heating portion of the heating member, the surface of the heating portion of the heating member abuts the inner wall of the hollow portion of the oxygen sensing element.

When the center line of the heating member is eccentric (offset) to the center line of the hollow portion of the oxygen sensing element, a portion of the oxygen sensing element closer to the heating member is heated to a greater extent, and the heat distribution over the circumference of the oxygen sensing element may not be uniform. According to conventional design concepts, such a sensor construction involving nonuniform heating of the oxygen sensing element will conceivably consume significant time until the overall electrical resistance of the oxygen sensing element becomes sufficiently low, potentially resulting in prolongation of a rise time of the sensor. However, the inventors of the present invention determined that the seemingly undesirable construction described above reduces the activation time of the oxygen sensor to that of a conventional sensor or shorter.

Through employment of a laterally-abutting structure in which the heating portion of the heating member laterally abuts the inner wall of the hollow portion of the oxygen sensing element, heat generated in the heating portion is directly transferred from the heating member to the oxygen sensing element through the contact portion. Heat radiated from a portion around the contact portion heats the oxygen sensing element in a supplementary manner. Therefore, the oxygen sensing element is heated swiftly. That is, the activation time of the sensor is reduced. If the heating portion and the oxygen sensing element undergo thermal expansion, the structure in which the heating portion of the oxygen sensing element laterally abuts the inner wall of the hollow portion of the oxygen sensing element is less affected by the thermal expansion than the structure in which the extreme end of the heating portion abuts the inner surface of the extreme end of the oxygen sensing element. In other words, even when the heating portion and the oxygen sensing element are subjected to a heat history, the laterally-abutting structure can retain good contact therebetween.

In the structure in which the heating portion of the heating member laterally abuts the inner wall of the hollow portion of the oxygen sensing element, direct heat transfer owing to the contact and the radiation heat transfer cooperate to provide more efficient heat transfer than in the case of the end-to-end contact structure. The fact that stable contact between the oxygen sensing element and the beating portion of the heating member is ensured leads to lessening of the nonuniformity of the heat distribution over the oxygen sensing element, and hence the lessening of the variation of the characteristics among individual oxygen sensors.

The above-described eccentric disposition of the heating member is implemented in the following manner. The positioning projection formed on the fixture portion of the fixture member and/or the heating-member holding portion abuts the peripheral surface of the heating member, whereby the heating member is eccentrically positioned within the hollow portion of the oxygen sensing element. When the fixture member is formed by, for example, plate work, such a positioning projection can be easily formed by press work.

The amount of eccentricity of the axis of the heating member with respect to the axis of the hollow portion can be easily adjusted through adjustment of the projection height.

The electrode layers may be respectively layered on the inner and outer surfaces of the oxygen sensing element. In this case, the electrode layers are electrodes (for example, Pt porous electrodes) having a reversible catalytic function (oxygen dissociation catalytic function) in relation to a dissociation reaction of oxygen molecules for injecting oxygen into the solid electrolyte of the oxygen sensing element and a recombination reaction of oxygen to cause the solid electrolyte to emit oxygen. The reason why, if the oxygen sensing element is locally heated, a rise time of the sensor is retained at a value substantially equal to or even less than that of the rise time of the conventional sensor, may be estimated as described below.

The oxygen sensor of this type operates in the following manner. A reference gas, such as air, is introduced into the interior of the oxygen sensing element, and a gas to be measured, such as an exhaust gas, is applied onto the outside of the oxygen sensing element. The oxygen concentration in a gas under measurement is detected with reference to an electromotive force, which is generated in the oxygen sensing element depending on a difference between the oxygen concentrations inside and outside the oxygen sensing element. In order to cause the oxygen sensing element constructed with oxygen ion conductive solid electrolyte to produce a sufficient electromotive force, the electric resistance of the oxygen sensing element must be sufficiently low, and the catalytic activity of the porous electrodes in relation to the dissociation and the recombination reaction of oxygen molecules must be sufficiently high. An output level of the oxygen sensor is determined depending on a tradeoff between the electrical resistance of the oxygen sensing element and the catalytic activity of the porous electrodes.

The catalytic activity of the porous electrode made of Pt, for example, conceivably tends to increase to a greater extent in response to temperature than does oxygen ion mobility of a solid electrolyte of a $ZrO_2$ group, for example. When the oxygen sensing element is locally heated through employment of the structure of the present invention, a reduction in the electric resistance of the oxygen sensing element effected through activation of the solid electrolyte is less intensive due to nonuniform heating, in relation to the case of the conventional structure in which the oxygen sensing element is disposed coaxially with the heating member. In this case, a heated portion of the oxygen sensing element is higher in temperature than in the conventional structure, so that the catalytic activity is increased at the portions of the porous electrodes corresponding in position to the heated portion. With the increase of the catalytic activity of the porous electrodes, dissociation of oxygen molecules in the gas under measurement is promoted, so that the electromotive force of the solid electrolyte and hence the output level of the sensor are increased, and the rise time of the sensor becomes equal to or shorter than in the case of the conventional structure.

In an oxygen sensor according to another embodiment of the invention, the heating member is disposed such that the entirety of the center line thereof disposed within the hollow portion of the oxygen sensing element is accommodated within any one of four regions defined as follows. The hollow portion of the oxygen sensing element is divided into four regions by a first imaginary plane which includes the axis of the hollow portion and a second imaginary plane which includes the axis of the hollow portion and is orthogonal to the first imaginary plane. In other words, the above-defined first and second imaginary planes can be set such that the entirety of the axis of the hollow portion disposed within the hollow portion is accommodated within any one of four regions defined thereby.

Actions and effects yielded by the construction feature described above will be described with reference to FIG. 15. For convenience of description, the heating portion (42) is formed at an end portion of the heating member (3) which is inserted into the oxygen sensing element (2); and the inner wall (2a) of the hollow portion of the oxygen sensing element (2) is substantially cylindrical (in manufacture of the oxygen sensing element (2) through molding and firing of solid electrolyte powder, for easy release from a mold after molding, the inner wall surface (2a) of the hollow portion may be tapered such that the diameter thereof diminishes toward the bottom thereof. FIG. 15(c) depicts an instance where no matter how the first and second imaginary planes P1 and P2 are set, the axis O1 of the heating member (3) cannot be accommodated within any one of the four regions defined within the hollow portion by planes P1 and P2. Since the axis O1 is considerably inclined in relation to the axis O2 of the oxygen sensing element (2), the center axis O1 unavoidably passes through at least two of the four regions. FIG. 15(a) depicts a case where, through appropriate setting of the first and second imaginary planes P1 and P2, the axis O1 of the heating member (3) can be accommodated within any one of the four regions. In this case, the inclination of the axis O1 of the heating member (3) in relation to the center axis O2 of the oxygen sensing element (2) is smaller than in the case of FIG. 15(c).

In the construction shown in FIG. 15(c), an end corner part of the heating portion (42) is located closer to the inner wall (2a) of the hollow portion of the oxygen sensing element (2) than is the remaining part of the heating portion (42). As a result, to some extent heating tends to concentrate on a portion of the inner wall (2a) which faces the end corner part. In the construction of FIG. 15(a), according to an embodiment of the invention, the inclination of the axis O1 of the heating member (3) in relation to the axis O2 of the oxygen sensing element (2) is smaller than that in the construction of FIG. 15(c). Thus, a side wall of the heating portion (42) substantially extends along the inner wall (2a) of the hollow portion of the oxygen sensing element (2), so that the heating portion (42) can more uniformly heat a wall portion of the oxygen sensing element (2). Therefore, a significant effect can be expected in terms of a reduction in the activation time of the oxygen sensor. Even in the construction of FIG. 15(c), since the axis O1 of the heating member (3) is eccentric to the axis O2 of the oxygen sensing element (2), a certain effect can also be expected in terms of a reduction in the activation time of the oxygen sensor.

In the construction of FIG. 15(b), the heating member (3) is disposed within the hollow portion of the oxygen sensing element (2) such that the axis O1 of the heating member (3) is substantially parallel to the axis O2 of the hollow portion. This construction further enhances the effect that the side wall of the heating portion (42) extends along the inner wall (2a) of the hollow portion of the oxygen sensing element (2), in terms of uniform heating of the wall portion of the oxygen sensing element (2).

In the fixture member, the positioning projection may be provided at either or both of the heating-member holding portion or the fixture portion. When the positioning projection is provided at the fixture portion and either one of the heating-member holding portions with which the fixture portion can be coupled is eliminated, the length of the fixture member along the axial direction of the heating member can be reduced. Accordingly, the oxygen sensor is reduced in length along the axial direction of the heating member and hence becomes more compact. Since the heating member is held by a single heating-member holding portion, the heating member is less susceptible to an excessive lateral force which might otherwise be applied thereto via the fixture member when the heating member equipped with the fixture member is inserted into the hollow portion of the oxygen sensing element during sensor assembly work. Thus, for example, potential breakage of the heating member can be prevented during sensor assembly work.

In the thus-configured fixture member, the heating-member holding portion to be eliminated may be either one; i.e., the one disposed on the far side of the fixture portion along the axial direction of the heating member or that disposed on the near side. However, preferably, the heating-member holding portion on the far side with respect to the heating portion of the heating member is eliminated. In other words, in the fixture member, the heating-member holding portion is coupled with the fixture portion only on the near side with respect to the heating portion of the heating member. This construction frees the heating member from a grip on the far side, which is susceptible to an external force exerted through, for example, a sensor output terminal portion, and relieves a potentially exerted lateral force, thereby further effectively preventing, for example, breakage of the heating member. More specifically, according to an embodiment of the invention, the positioning projection is provided on the fixture portion in the vicinity of an end portion opposite that coupled with the heating-member holding portion and is located at a position corresponding to that where the heating-member holding portion is coupled with the fixture portion. This construction feature extends the distance in the axial direction of the heating member between a support point (abutment point) associated with the positioning projection and a support point associated with the heating-member holding portion, so that the fixture member can position and support the heating member.

The oxygen sensor according to another embodiment of the invention includes an oxygen sensing element of a hollow shaft-like member which is closed at the extreme end and has electrode layers on the inner and outer sides thereof, and a shaft-like heating member disposed within a hollow portion of the oxygen sensing element and adapted to heat the oxygen sensing element. The heating member is disposed such that the entirety of the axis thereof disposed within the hollow portion of the oxygen sensing element is accommodated within any one of four regions defined as follows. The hollow portion of the oxygen sensing element is divided into four regions by a first imaginary plane which includes the axis of the hollow portion and a second imaginary plane which includes the axis of the hollow portion and is orthogonal to the first imaginary plane. Thus, the axis of the heating member becomes eccentric to the axis of the hollow portion.

An oxygen sensor according to a further embodiment includes an oxygen sensing element of a hollow shaft-like member which is closed at the extreme end and has electrode layers on the inner and outer sides thereof, and a shaft-like heating member disposed within a hollow portion of the oxygen sensing element and adapted to beat the oxygen sensing element. The heating member is disposed such that the center line thereof is disposed substantially parallel and eccentric to the center line of the hollow portion. Actions and effects yielded by the construction features described above are similar to those yielded by the construction features which have been described previously with reference to FIG. 15, and thus description thereof is omitted. In the constructions of present embodiment, a mechanism for establishing the eccentricity between the center line of the heating member and the center line of the hollow portion is not limited to the positioning projection employed in the embodiment first described.

In the structures according to the present embodiment, there can be provided a fixture member including a fixture portion circumferentially surrounding the heating member and directly or indirectly (i.e., via another member) maintaining contact with the inner wall of the oxygen sensing element, and a pair of heating-member holding portions coupled with the fixture portion at opposite sides as viewed in the axial direction of the heating member and adapted to hold the heating member. Through employment of the two heating-member holding portions, the heating member is held more stably.

In the structure according to the present embodiment, there can be provided a fixture member comprising a fixture portion circumferentially surrounding the heating member and directly or indirectly (i.e., via another member) maintaining contact with the inner wall of the oxygen sensing element, and a heating-member holding portion coupled with the fixture portion only at a near end with respect to the extreme end of the heating member as viewed in the axial direction of the heating member and adapted to hold the heating member. Through employment of a single heating-member holding portion, some degree of freedom is imparted to the heating member in terms of movement orthogonal to the axis of the heating member while the heating member is held by the heating-member holding portion. When the heating member equipped with the fixture member is inserted into the hollow portion of the oxygen sensing element, the end portion of the heating member maintains contact with the inner wall of the oxygen sensing element and is positioned along the inner wall. This positioning feature yields a significant effect in terms of a reduction in the activation time of the oxygen sensor. During sensor assembly work, the heating member is less susceptible to an excessive lateral force which might otherwise be applied thereto via the fixture member, thereby preventing, for example, potential breakage of the heating member during sensor assembly work. Further, since the length of the fixture member along the axial direction of the heating member can be reduced, the oxygen sensor is reduced in length along the axial direction of the heating member and hence becomes more compact.

In the construction according to another embodiment of the invention, the heating-member holding portion(s) can be coupled with the fixture portion such that the heating member is disposed in the following manner. The entirety of the center line of the heating member disposed within the hollow portion of the oxygen sensing element is accommodated within any one of four regions defined as follows. The hollow portion of the oxygen sensing element is divided into four regions by a first imaginary plane which includes the center line of the hollow portion and a second imaginary plane which includes the center line of the hollow portion and is orthogonal to the first imaginary plane. In other words, the heating-member holding portion(s) can be coupled with the fixture portion such that the center line thereof is disposed substantially parallel and eccentric to the center line of the hollow portion of the oxygen sensing element.

The fixture member may serve as a terminal member which includes an internal electrode connecting portion maintaining contact with the electrode layer on the inner side of the oxygen sensing element, and the fixture portion may serve as the internal electrode connecting portion. As a result of the fixture portion serving as the internal electrode connecting portion for outputting a signal from the oxygen sensing element, the number of component parts is reduced, so that the oxygen sensor can be fabricated at low cost and in a simplified assembly procedure.

In the present invention, the following structure may be used: the heating member is disposed eccentric to the oxygen sensing element, but the surface of the heating portion of the heating member is disposed in proximity to the inner wall of the hollow portion of the oxygen sensing element, viz., is not in contact with the latter. By employment of this structure, more heat is radiated from the heating portion to the oxygen sensing element than in the case of the structure in which the heating member is disposed coaxial with the oxygen sensing element. This also contributes to reduction in the activation time of the oxygen sensor.

In the oxygen sensor of the present invention, the difference $\Delta D$ between the internal diameter DA of a cross section of the oxygen sensing element and the external diameter DB of a cross section of the heating member; i.e., $\Delta D=DA-DB$, is preferably not greater than 0.35 mm. The internal diameter of a cross section of the oxygen sensing element and the external diameter of a cross section of the heating member, respectively, indicate the inside diameter of the oxygen sensing element and the outside diameter of the heating member when the inner surface of the oxygen sensing element and the outer surface of the heating member are cylindrical surfaces. When the inner surface of the oxygen sensing element and the outer surface of the heating member are not circular in cross section, they are converted into surfaces circular in cross section while respective areas are held unchanged, and the inside diameter and the outside diameter of the thus-converted circular cross sections are used. When the diameter of the cross section varies along the axial direction (for example, the inner surface of the oxygen sensing element or the outer surface of the heating member is tapered in the axial direction), an average value of diameters as calculated with respect to the axial direction is used.

If $\Delta D$ (=DA−DB) exceeds 0.35 mm, the activation time of the oxygen sensing element and hence the sensor rise time are increased, or the rise time tends to vary among individual oxygen sensors. The reason for this may be estimated such that, when the heating member is caused to laterally abut the inner wall of the hollow portion of the oxygen sensing element, if the difference $\Delta D$ is large, a force for abutting the heating member and the inner wall of the oxygen sensing element tends to vary among individual oxygen sensor products. More preferably, the difference $\Delta D$ is not greater than 0.30 mm. If the difference $\Delta D$ is less than 0.1 mm, inserting the heating member into the oxygen sensing element becomes difficult, thus impairing the efficiency of assembling the heating member to the oxygen sensing element. For this reason, the difference $\Delta D$ is preferably not less than 0.1 mm and more preferably not less than 0.15 mm.

The ratio ($\Delta D/DB$) of the difference $\Delta D$ (the difference $\Delta D$ between the internal dimension DA of a cross section of the oxygen sensing element and the external dimension DB of a cross section of the heating member; $\Delta D=DA-DB$) to the external diameter DB is preferably not greater than 0.13. When the ratio $\Delta D/DB$ exceeds 0.13, the sensor rise time increases, or the characteristics of individual oxygen sensors tend to become nonuniform. Therefore, the ratio $\Delta D/DB$ is more preferably set to not greater than 0.10.

The features according to another embodiment of the invention are particularly effective when applied to the construction previously described, in which the heating member is held by only a single heating-member holding portion. Specifically, through adjustment of ΔD or ΔD/DB to the above range, the extreme end of the heating member is more readily positioned along the inner wall of the hollow portion of the oxygen sensing element when it is brought in contact with the inner wall and inserted into the hollow portion along the inner wall. Thus, the activation time of the oxygen sensor is more effectively reduced.

When the heating portion of the heating member has a region, at a circumferential position, where heat distribution is sparse, the heating portion of the heating member can be brought into contact with the inner wall of the hollow portion of the oxygen sensing element such that other region maintains contact with the inner wall. For example, when the heating portion is formed by the steps of printing a heat-generating resistor pattern on a ceramic green sheet, rolling round the resultant sheet into a core member, and sintering the member, the heat-generating resistor pattern becomes sparse in a seam region where the ends of the ceramic green sheet abut each other. The region of the heating portion opposite the seam region is preferably brought into contact with the inner wall of the oxygen sensing element. Even when the region of sparse heat distribution is brought into contact with the inner wall of the oxygen sensing element, a certain amount of heat transfer is effected. However, when a region of sufficient heat generation is brought into contact with the inner wall of the oxygen sensing element, more effective heat transfer is achieved. Because of nonuniform distribution of heat generation along the circumferential direction, thermal energy is concentrated in a smaller volume. This unique feature is particularly effective for attaining a reduction in the activation time after current is applied to the heater.

The heating portion of the heating member may be located in proximity to an extreme end of the heating member. This unique feature is effective for swiftly heating the oxygen sensing element. The heating portion may be formed over the entire surface of the heating member. In this case, thermal energy tends to disperse. To secure effective heating of the oxygen sensing element, the heating portion is preferably located in proximity to an end of the heating member, since heat is generated locally or in a local region. The locally-generated heat and the laterally-abutting structure realized by the eccentric disposition cooperate to further reduce the activation time of the oxygen sensor.

In the present invention, the heating member may be assembled into the oxygen sensing element by means of the fixture member, and the heating portion of the heating member may be pressed against the inner wall of the hollow portion of the oxygen sensing element by the fixture member. This feature makes the laterally-abutting structure stable and further suppresses a characteristic variation among individual oxygen sensor products.

The fixture member used in the present invention may include a constricted coupling part for coupling the fixture portion and the heating-member holding portion. Provision of the constricted coupling part provides, for example, the following advantage. When the heating member is to be deformed by thermal stress generated therein, the coupling part is elastically or plastically deformed to thereby reduce the thermal stress and hence suppress potential damage to the heating member.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Embodiments of the present invention will be described with reference to the accompanying drawings.

Figure 1:
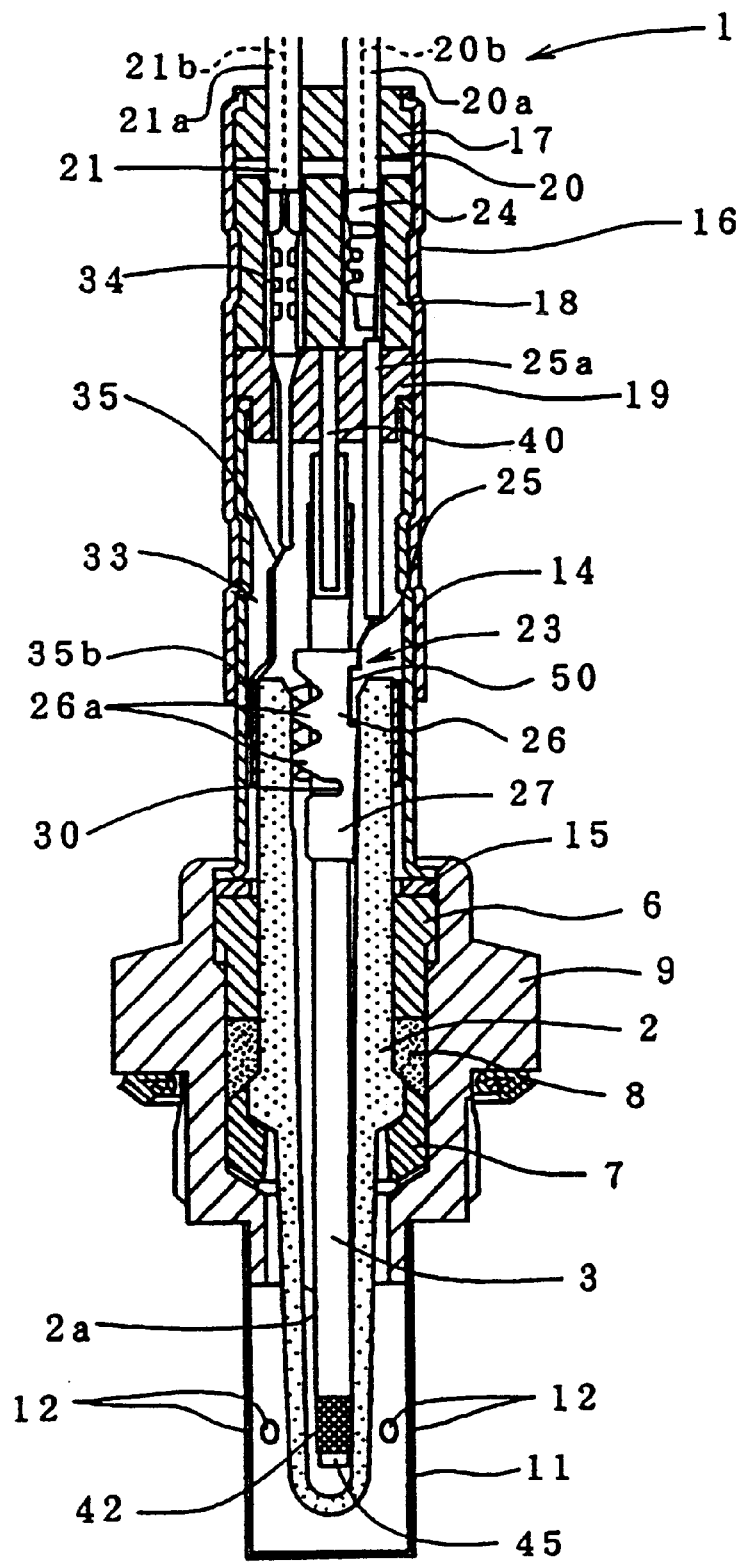
FIG. 1 shows a longitudinal sectional view showing an oxygen sensor according to an embodiment of the present invention.

FIG. 1 shows an oxygen sensor 1 according to an embodiment of the invention. The oxygen sensor 1 is assembled from an oxygen sensing element 2, a shaft-like heating member 3, and various members forming an outer shell covering them. The oxygen sensing element 2 is a hollow shaft-like member formed of solid electrolyte and having a closed end. The shaft-like heating member 3 is a ceramic heater. The oxygen sensing element 2 is made of oxygen-ion conductive solid electrolyte. A typical example of the solid electrolyte is a solid solution of $ZrO_2$ containing $Y_2O_3$ or CaO, or a solid solution of $ZrO_2$ and an oxide of an alkaline-earth metal or a rare-earth metal. $HfO_2$ may be contained in $ZrO_2$ serving as a base.

Figure 2:
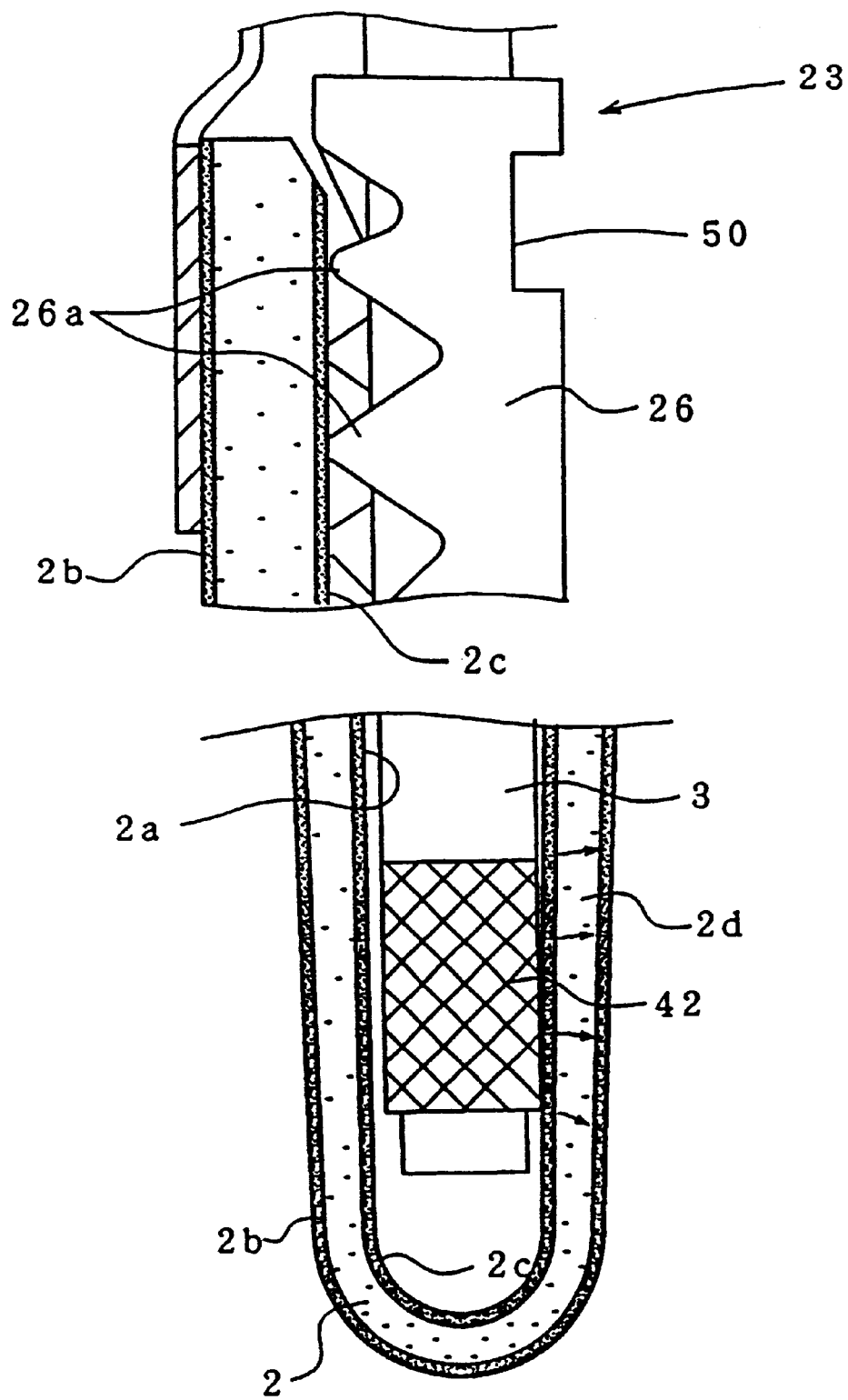
FIG. 2 shows an enlarged, cross-sectional view showing the contact portion of a heating portion and an oxygen sensing element of the embodiment shown in FIG. 1.

The oxygen sensing element 2 is disposed passing through a housing 9 serving as a metal tubular member while being electrically insulated from the housing 9. Specifically, the housing 9 is disposed around the middle of the oxygen sensing element 2 in a state that insulators 6 and 7 of insulating ceramic and a ceramic powdery material 8 of talc are inserted therebetween. As shown in FIG. 2, electrode layers 2b and 2c are layered entirely over the inner and outer surfaces of the oxygen sensing element 2, respectively. The electrode layers 2b and 2c are electrodes, for example, Pt porous electrodes, having a reversible catalytic function (oxygen dissociation catalytic function) in relation to a dissociation reaction of oxygen molecules for injecting oxygen into the solid electrolyte of the oxygen sensing element 2 and a recombination reaction of oxygen to cause the solid electrolyte to emit oxygen.

Referring again to FIG. 1, protector 11 is placed at one of the open ends of the housing 9, while covering the extreme end of the oxygen sensing element 2 with a space intervening therebetween. A plurality of gas holes 12 through which exhaust gas passes are formed in the protector 11. Through the gas holes 12, oxygen contained in the exhaust gas maintains contact with the surface of the tip end of the oxygen sensing element 2. A first sleeve 14 is fit to and caulked at the other open end of the housing 9 in a state that a ring 15 is placed between it and the insulator 6. A second sleeve 16 is fit and fixed to the first sleeve 14. The upper opening of the second sleeve 16 in FIG. 1 is sealed with a plug 17. Further, plugs 18 and 19 are located under the plug 17 within the second sleeve 16. Lead wires 20 and 21 are provided passing through the plugs 17 and 18.

The lead wire 20 is electrically connected to the inner electrode layer, not shown, of the oxygen sensing element 2 through a connector portion 24 of a terminal member 23 (which serves as the fixture member), a lead-out strip portion 25 (covered with an insulating tube 25a) connected to the connector portion 24, and an internal electrode connecting portion 26 (which serves as the fixture portion) of the terminal member 23. The lead wire 21 is electrically connected to the outer electrode layer, not shown, of the oxygen sensing element 2 through a connector portion 34, a lead-out strip portion 35 connected to the connector portion 34, and an external electrode connecting portion 35b of another terminal member 33. A pair of positive and negative heater terminals 40 for feeding current to the heating member 3 are fixed to the base (upper end in FIG. 1) of the heating member 3, and via the heater terminals 40, current is fed to a heating resistor circuit (to be described later) embedded in the heating member 3. The pair of heater terminals 40 are connected to a pair of lead wires (not shown) for the heater that penetrate the plugs 17 and 18.

In the oxygen sensor 1 according to the present embodiment, air as base gas is introduced into a space within the oxygen sensing element 2 through, for example, gaps formed between sheaths 20a and 21a and cores 20b and 21b of the lead wires 20 and 21. Exhaust gas is introduced through the gas holes 12 of the protector 11 and comes in contact with the outer surface of the oxygen sensing element 2. As a result, an electromotive force is generated in the oxygen sensing element 2 by oxygen concentration cell effect. The generated electromotive force depends on the oxygen concentration difference between the interior and the exterior of the oxygen sensing element 2. The electromotive force is lead out through the lead wires 20 and 21 from the electrode layers 2b and 2c, in the form of a detecting signal representative of the oxygen concentration contained in the exhaust gas. When the exhaust gas temperature is sufficiently high, the oxygen sensing element 2 is heated by the exhaust gas, so that it is activated. When the exhaust gas is at low temperature, upon engine startup for example, the oxygen sensing element 2 is forcibly heated by the heating member 3 to be activated.

Figure 5:
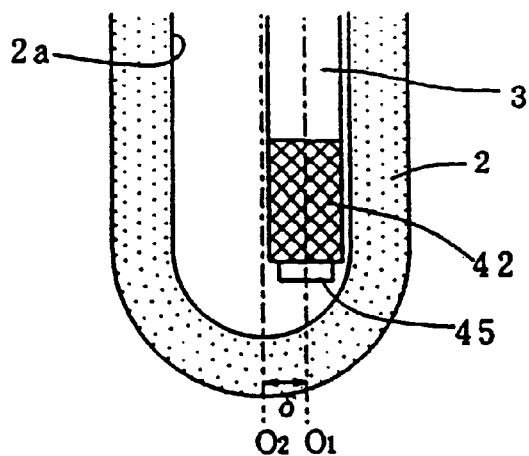
FIG. 5 shows a partial cross-sectional view conceptually showing a main portion of the embodiment shown in FIG. 2.
Figure 7:
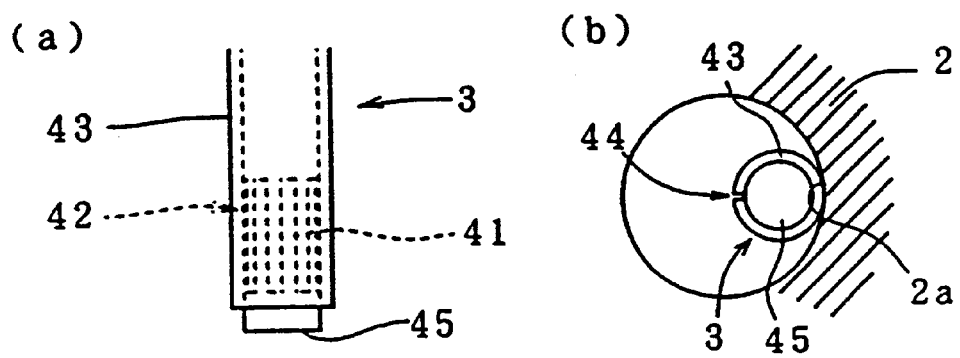
FIG. 7 shows an example of the heating portion shown in FIG. 1.

The heating member 3 is typically a ceramic heater. In the ceramic heater, a ceramic bar 45 made mainly of alumina is used as a core member. As shown in FIG. 5, a heating portion 42 is formed on the surface of the ceramic bar 45. The heating portion 42 includes a resistor wire part (resistor pattern) 41 patterned in a zigzag fashion (FIG. 7). A predetermined pattern of resistor paste is printed on a sheetlike outer ceramic portion 43 (FIG. 7). The outer ceramic portion 43 is rolled round the ceramic bar 45 and sintered. The ceramic bar 45 is slightly projected outside from the extreme end of the outer ceramic portion 43. Current is fed to the resistor pattern 41 through a current passage, not shown, extended from the heater terminals 40. The heating portion 42 is located at a portion of the heating member 3 close to the extreme end thereof. Accordingly, heat is generated locally or in the extreme end portion of the heating member.

As shown in FIG. 5, in the vicinity of the heating portion 42 of the heating member 3, the axis O1 of the heating member 3 is eccentric to (offset with respect to) the axis O2 of the oxygen sensing element 2 by a fixed distance δ. The surface of the extreme end of the heating portion 42 of the heating member 3 is in contact with the inner wall (referred also to as an element inner wall) 2a of the hollow portion of the oxygen sensing element 2, while being pressed against the element inner wall at predetermined surface pressure. As shown in FIG. 1, the contact position of the heating portion 42 is preferably offset to some extent from the closed end of the oxygen sensing element 2 toward the middle of the oxygen sensing element 2, more preferably located at a position substantially corresponding to the gas holes 12 of the protector 11.

Figure 15:
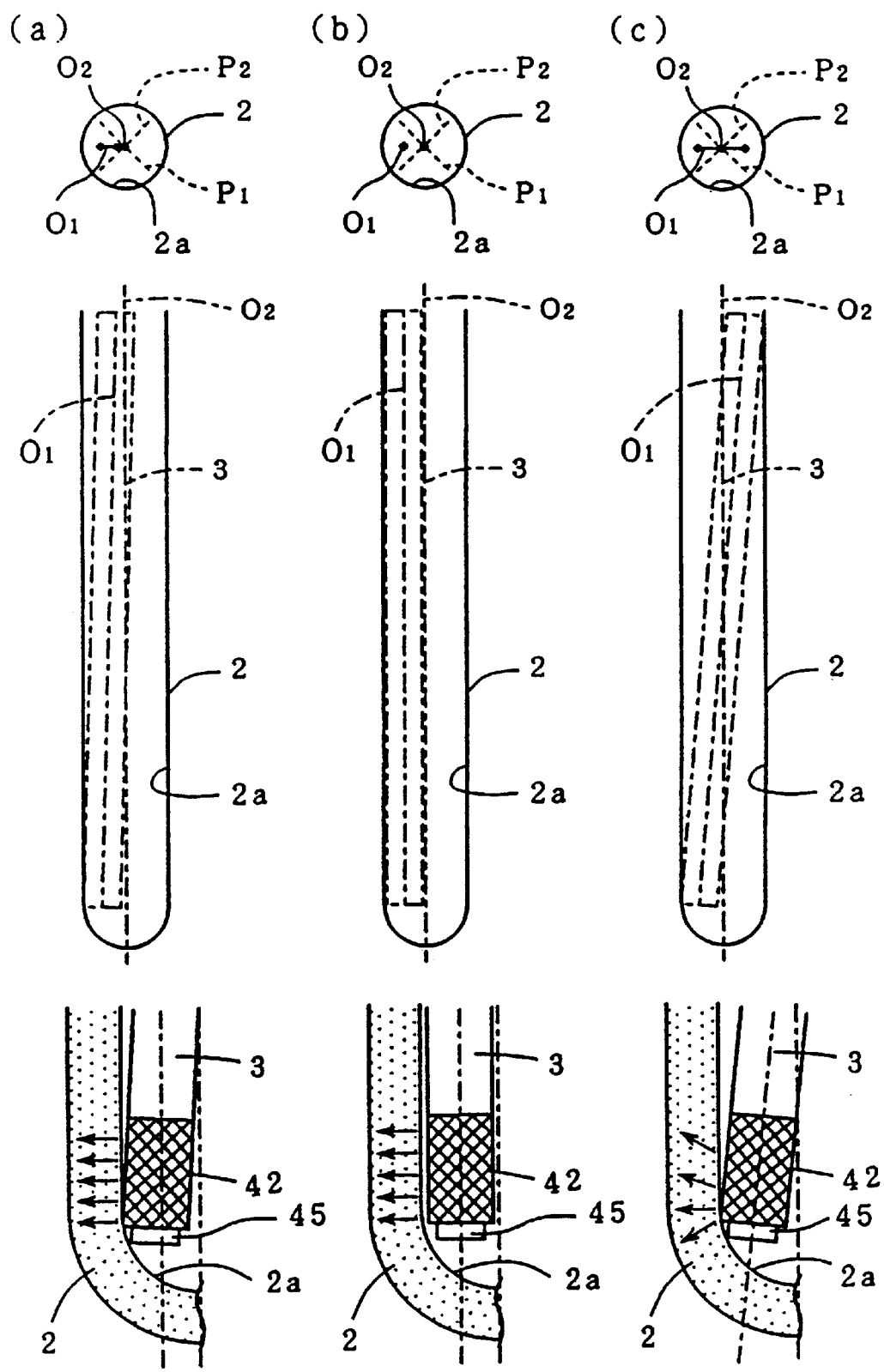
FIGS. 15(a)–(c) show a conceptual view depicting operation of the oxygen sensor of the present invention through use of examples.

As schematically shown in FIG. 15(b), the heating member 3 is disposed in the following manner. The entirety of the axis O1 of the heating member 3 disposed within the hollow portion of the oxygen sensing element 2 is accommodated within any one of four regions defined as follows. The hollow portion of the oxygen sensing element 2 is divided into four regions by a first imaginary plane P1 which includes the axis O2 of the hollow portion and a second imaginary plane P2 which includes the axis O2 of the hollow portion and is orthogonal to the first imaginary plane P1. In other words, as shown in FIG. 5, the heating member 3 is disposed within the hollow portion such that the axis O1 thereof is substantially parallel to the axis O2 of the hollow portion, and hence such that a side wall of the heating portion 42 substantially extends along the element inner wall 2a.

The terminal member 23 functions to offset the axis O1 of the heating member 3 from the axis O2 of the hollow portion of the oxygen sensing element 2 as described above and to elastically press the heating portion 42 of the heating member 3 against the element inner wall 2*a*. In this case, the terminal member 23 has three functions. First, the terminal member 23 serves as an output terminal of the inner electrode layer of the oxygen sensing element 2 and electrically connects the oxygen sensing element 2 to the lead wire 20. Second, the terminal member 23 fixes the heating member 3 to the inside of the oxygen sensing element 2. This function is the same as that of the conventional sensor. Third, the terminal member 23 elastically presses the extreme end of the heating member 3 against the element inner wall 2*a* to form the laterally-abutting structure.

Figure 3:
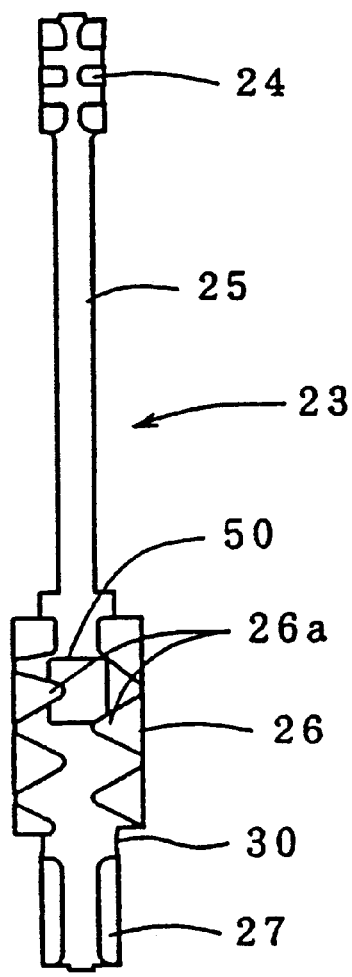
FIGS. 3(a) and 3(b) show the terminal member of FIG. 1 in greater detail.
Figure 3:
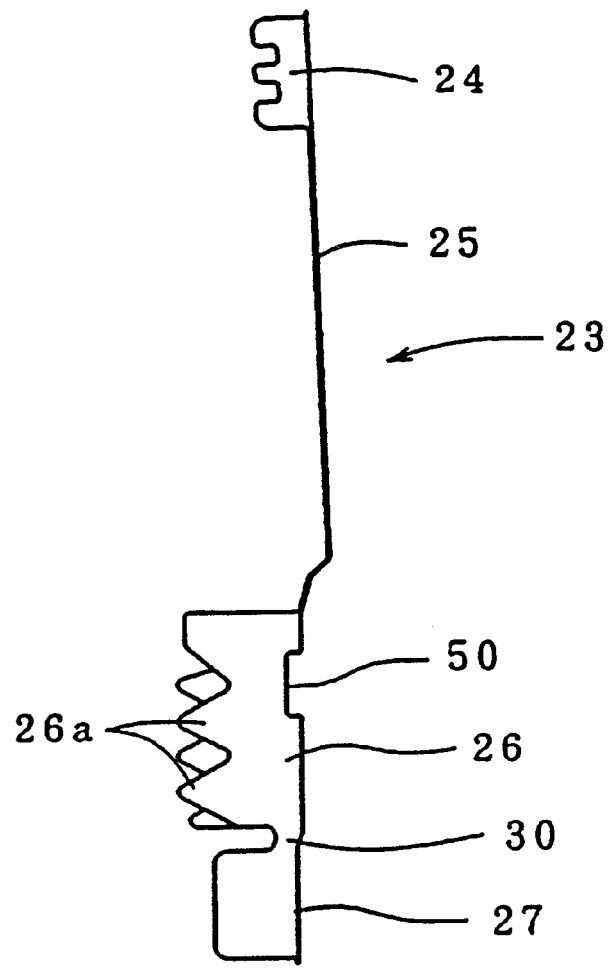
Figure 4:
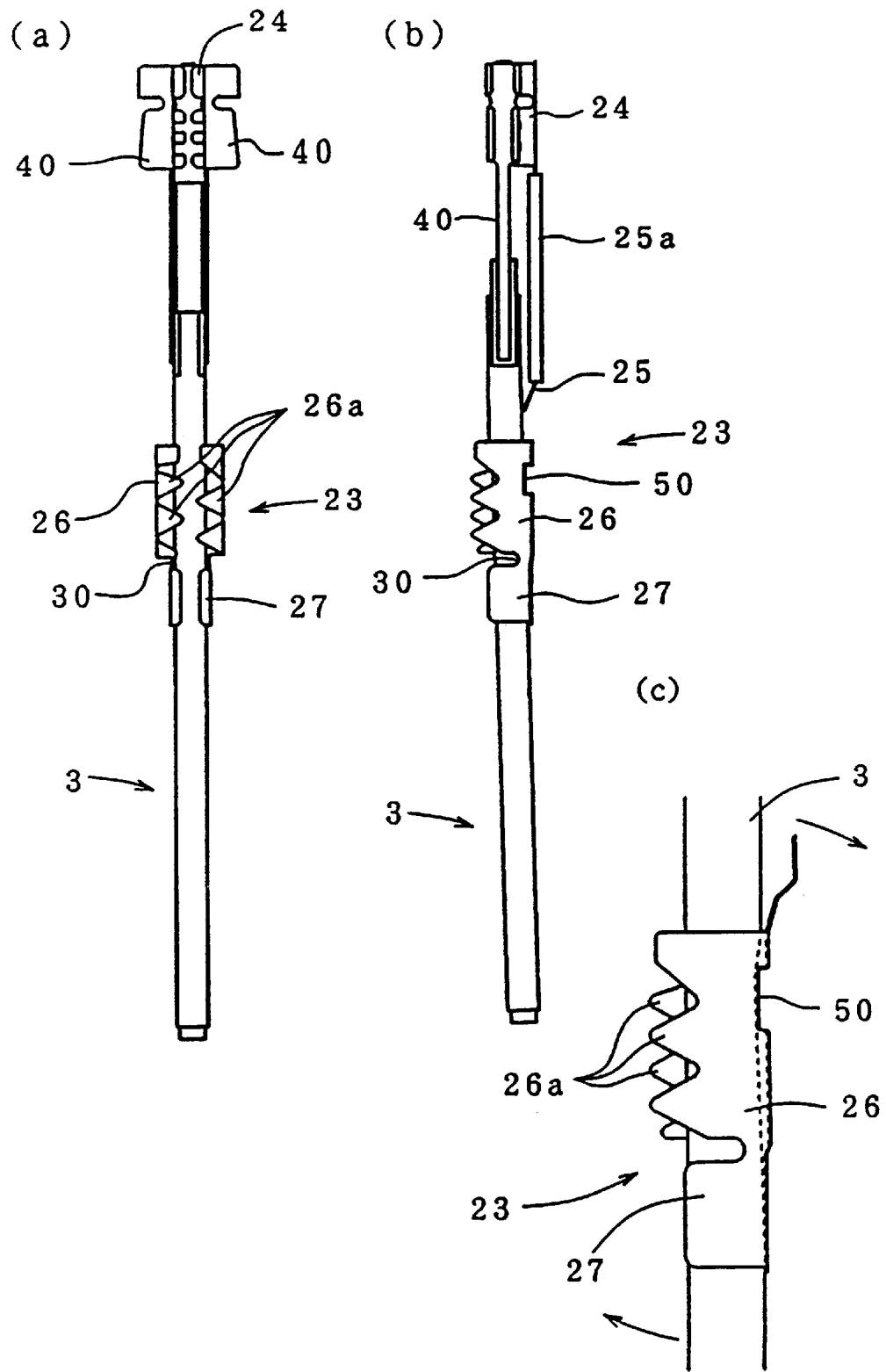
FIGS. 4(a) and 4(b) show an assembly of the terminal member of FIGS. 3(a) and 3(b) and a heating member.

FIG. 3 shows the terminal member 23 alone, and FIG. 4 shows the terminal member 23 and the heating member 3 being assembled. As seen from these figures, the internal electrode connecting portion 26 of the terminal member 23 includes a heating-member holding portion 27 located at the near end with respect to the extreme end of the heating member 3 (i.e., at the near side with respect to the heating portion 42). The heating-member holding portion 27 is shaped in a letter C in cross section to surround the heating member 3. The heating-member holding portion 27 has an internal diameter slightly smaller than the external diameter of the heating member 3 when the heating member 3 is not inserted thereinto. When the heating member 3 is inserted into the heating-member holding portion 27, the internal diameter of the heating-member holding portion 27 elastically expands to thereby hold the heating member 3 by means of a frictional force exerted therebetween. The heating-member holding portion 27 is provided at only one axial end of the internal electrode connecting portion 26.

In order to form the internal electrode connecting portion 26, a blank sheet portion having saw-tooth contact parts 26*a* formed at opposite side edges are bent into a cylindrical form, which may surround the heating member 3. The internal electrode connecting portion 26 functions to axially position the heating member 3 within the hollow portion of the oxygen sensing element 2 by means of a frictional force exerted between the outer surface thereof and the inner wall 2*a* of the hollow portion. Electrical connection with the inner electrode layer 2*c* (FIG. 2) is established by means of tip portions of the contact parts 26*a*. A predetermined gap intervenes between the internal electrode connecting portion 26 and the heating member 3. The saw-tooth contact parts 26*a* of the internal electrode connecting portion 26 are staggered such that the tops of one saw profile are aligned with the bottoms of the other saw profile. Through employment of this staggered feature, during sensor assembly work, when the internal electrode connecting portion 26 is inserted into the oxygen sensing element 2, it rarely happens that the opposite saw-tooth contact parts 26*a* are caught at the edge of the open end of the oxygen sensing element 2. This facilitates assembling of the internal electrode connecting portion 26 and the oxygen sensing element 2. It is preferable that the height of the saw-tooth contact parts 26*a* be increased to some extent. This increases the width of the blank sheet portion as viewed in the bending direction, thereby facilitating the work of bending the blank sheet portion into the internal electrode connecting portion 26.

A positioning projection 50 is provided on the internal electrode connecting portion 26 in the vicinity of an end portion opposite that coupled with the heating-member holding portion 27 and is located at a position corresponding to that of a coupling part 30 where the heating-member holding portion 27 is coupled with the internal electrode connecting portion 26. The positioning projection 50 is projected inward and is adapted to abut the peripheral surface of the heating member 3. The positioning projection 50 is formed by, for example, concaving the wall of the internal electrode connecting portion 26, and is intended to position the heating member 3 while the heating member 3 is eccentric to the axis O2 of the hollow portion of the oxygen sensing element 2.

In order to attain good mold release when the oxygen sensing element 2 is fabricated from a solid electrolyte powder through molding and sintering, the inner wall 2*a* of the hollow portion of the oxygen sensing element 2 is slightly tapered such that the diameter thereof diminishes toward the bottom of the hollow portion. As shown in, for example, FIG. 5, the heating member 3 is disposed within the hollow portion such that the axis O1 thereof is substantially parallel to the axis O2 of the oxygen sensing element 2. Thus, the gap formed between the heating member 3 and the element inner wall 2*a* must be axially increased toward the base end of the heating member 3. The positioning projection 50 is adapted to establish the gap of a predetermined value at the position thereof, so that the heating portion 42 of the heating member 3 is in contact with the element inner wall 2*a* while the axis O1 is substantially parallel to the axis O2.

In fabrication of the oxygen sensor 1, it is a common practice that after the terminal member 23 is fixed to the heating member 3, the resultant assembly is inserted into the oxygen sensing element 2. Assuming that a wall portion of the oxygen sensing element 2 exerts no restraint on the heating member 3, the positional relationship in the radial direction between the heating-member holding portion 27 and the internal electrode connecting portion 26 is determined in the following manner. The heating-member holding portion 27 and the positioning projection 50 cooperatively holds the heating member 3 in such a slightly inclined fashion that a portion of the axis O1 of the heating member 3 corresponding to the heating portion 42 is offset more with respect to the axis O2 of the hollow portion of the oxygen sensing element 2 than is the remainder of the axis O1. Through employment of this feature, when the assembly is inserted into the oxygen sensing element 2, an end portion of the heating member 3 slides on the element inner wall 2*a* while being in elastic contact with the element inner wall 2*a*. As a result, as represented by the arrows of FIG. 4(*c*), the assembly is installed into the oxygen sensing element 2 while the inclined state of the heating member 3 is corrected so that the axis O1 of the heating member 3 becomes parallel to the axis O2 of the hollow portion. Between the heating-member holding portion 27 and the internal electrode connecting portion 26, the terminal member 23 is circumferentially cut out from both sides to form U-shaped cutouts or a constricted coupling part 30. When the assembly is inserted into the oxygen sensing element 2, the coupling part 30 elastically deforms inward. An elastically restoring force associated with the elastic deformation causes the heating portion 42 of the heating member 3 to be pressed against the inner wall 2*a* of the hollow portion of the oxygen sensing element 2, thereby establishing the laterally-abutting structure as shown in FIG. 1.

In this state, a stress exerted on the heating member 3 by the element inner wall 2*a*, a stress exerted on the heating member 3 at the positioning projection 50, and a stress exerted on the heating member 3 at the heating-member holding portion 27 are combined into a bending moment. A measure is taken to prevent the bending moment from breaking the heating member 3, in other words, to prevent generation of a stress in excess of a tolerable range of strength of the heating member 3. The constricted coupling part 30 adjacent to the internal electrode connecting portion 26 is adapted to adjust such a stress or such a bending moment.

The coupling part 30 also functions to absorb or lessen a bending force which is applied to the heating member 3 via the heating-member holding portion 27 and the positioning projection 50 in the above insertion step. The elastic force of the coupling part 30 can be adjusted through adjustment of the width of constriction. In other words, through appropriate adjustment of the width of constriction of the coupling part 30, the elastic force of the coupling part 30 can be adjusted. Thus, in the laterally-abutting structure of the heating member 3 shown in FIG. 1, the heating member 3 is pressed against the element inner wall 2*a* by a necessary and sufficient elastic force.

As shown in FIG. 7(*b*), when the outer ceramic portion 43 of the heating member 3 is rolled round the ceramic bar 45, a slit 44 is formed between the ends of the outer ceramic portion 43 while being axially extended. The resistor pattern 41 is absent along the slit 44 and its adjacent portions, and less heat is generated along these portions. Therefore, when the surface of the heating portion 42 is abutted against the element inner wall 2*a*, the portion of the heating portion surface opposite to the slit 44 side is preferably brought in contact with the element inner wall 2*a*. By so doing, heat is directly and efficiently transferred from the heating portion to the oxygen sensing element 2.

The inner wall 2*a* of the hollow portion of the oxygen sensing element 2 is tapered. A difference $\Delta D$ between an average value (referred to merely as an inside diameter) DA of the inside diameter of the oxygen sensing element 2 and the outside diameter DB of the heating member 3 is preferably 0.1 to 0.35 mm ($\Delta D = DA - DB$), and more preferably 0.15 to 0.30 mm. A ratio of the difference $\Delta D$ to the outside diameter DB of the heating member 3 is not greater than 0.13, preferably not greater than 0.10.

Operation of the oxygen sensor described 1 described above will next be described in detail.

Figure 6:
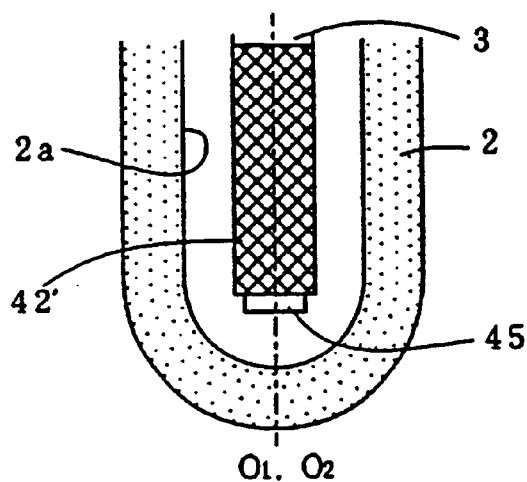
FIG. 6 shows a partial cross-sectional view conceptually showing a main portion of a conventional oxygen sensor.

FIG. 6 shows a structure of a conventional oxygen sensor, which corresponds to the already illustrated structure of the oxygen sensor of the invention. As shown in the conventional structure, the axis O1 of the heating member 3 is coaxial with the axis O2 of the oxygen sensing element 2. As seen from the comparison of the structure of FIG. 6 with that of FIG. 5, in the structure of the invention (FIG. 5), the axis O1 of the heating member 3 is disposed substantially parallel and eccentric to the axis O2 of the oxygen sensing element 2 by distance δ in a state that the surface of the extreme end of the heating portion 42 of the heating member 3 is pressed against the element inner wall 2*a*. The structure of the invention may be called a laterally-abutting structure. In FIGS. 5 and 6, for ease of understanding, the gap between the heating member 3 and the oxygen sensing element 2 is illustrated in an exaggerating manner. Actually, the offset distance $\Delta$ is, for example, approximately 0.085 to 0.385 mm when the inside diameter defined by the element inner wall 2*a* is 2.8 to 3.2 mm and the outside diameter of the heating member 3 is 2.43 to 2.63 mm. By so selecting, a reliable laterally-abutting structure is secured without giving rise to an excessive pressure between the heating member 3 and the oxygen sensing element 2. Further, it is noted that the heating portion 42 of FIG. 5 occupies a narrower region biased to the distal end portion of the heating member 3 than the heating portion 42' of FIG. 6.

The laterally-abutting structure in which the heating member 3 is brought in contact with the element inner wall 2*a*, according to the present embodiment, brings about many advantages. Heat generated in the heating portion 42 is swiftly transferred to the oxygen sensing element 2 and heats it. Heat radiated from a locally heated portion in the vicinity of the contact position of the heating portion 42 heats the oxygen sensing element 2 in a supplementary manner. The heat conduction and the heat radiation cooperate to quickly heat the oxygen sensing element 2, to thereby reduce the time taken till the oxygen sensing element 2 is heated to its activation temperature.

As shown in FIG. 2, the oxygen sensing element 2 is locally heated by the heating portion 42 that is disposed while being in contact with the inner wall 2*a* of the oxygen sensing element 2. A rise time of the oxygen sensor 1 is retained at a value substantially equal or less than the rise time of the conventional sensor shown in FIG. 6. The reason for this, as estimated by the inventors, follows. In order to cause the oxygen sensing element 2, constructed with oxygen-ion conductive solid electrolyte, to produce a sufficient electromotive force, the electric resistance of the oxygen sensing element 2 must be sufficiently low and the catalytic activity of the electrode layers 2*b* and 2*c* in relation to the dissociation and the recombination reaction of oxygen molecules must be sufficiently high. An output level of the oxygen sensor 1 is determined depending on a tradeoff between the electric resistance of the oxygen sensing element 2 and the catalytic activity of the electrode layers 2*b* and 2*c*.

When the oxygen sensing element 2 is locally heated by the heating portion 42 of the heating member 3, a reduction in the electric resistance of the oxygen sensing element 2 effected through activation of the solid electrolyte is less intensive than in the conventional structure of FIG. 6. In this case, as shown in FIG. 2, a locally heated portion 2*d* of the oxygen sensing element 2 is more intensively heated than is the other portion, so that the catalytic activity is increased at the portions of the electrode layers 2*b* and 2*c* corresponding in position to the heated portion 2*d*. With the increase of the catalytic activity of the electrode layer 2*b*, the dissociation of oxygen molecules in the gas under measurement is promoted, so that the electromotive force of the solid electrolyte and hence the output level of the oxygen sensor 1 are increased, and the activation time (rise time) of the oxygen sensor 1 is reduced.

The heating member 3 is disposed such that the axis O1 thereof is substantially parallel to the axis O2 of the oxygen sensing element 2. As a result, a side wall of the heating portion substantially extends along the inner wall 2*a* of the hollow portion of the oxygen sensing element 2. This feature enables the heating portion 42 to more uniformly heat the wall portion of the oxygen sensing element 2, thereby further effectively reducing the activation time of the oxygen sensor 1.

As shown in FIG. 1, the heating-member holding portion 27 is coupled with the internal electrode connecting portion 26 only at the near side with respect to the heating portion 42 of the heating member 3, so that the length of the terminal member 23 along the axial direction of the heating member 3 can be reduced. Accordingly, the oxygen sensor 1 is reduced in length along the axial direction of the heating member 3 and hence becomes more compact. Since the heating member 3 is held by a single heating-member holding portion 27, the heating member 3 is less susceptible to an excessive lateral force which might otherwise be applied thereto via the terminal member 23 when the heating member 3 equipped with the terminal member 23 is inserted into the hollow portion of the oxygen sensing element 2 during sensor assembly work. Thus, for example, potential breakage of the heating member 3 can be prevented during sensor assembly work.

In our experiment, the following facts were confirmed. In the conventional sensor structure as shown in FIG. 6, when a heater resistance value was 3 to 3.5Ω, approximately 20 seconds were taken until the sensor activation temperature was reached. In the case of the laterally-abutting structure shown in FIG. 5, at the same resistance value, approximately 15 seconds were taken till the activation temperature was reached when the heating member 3 was merely eccentrically disposed (i.e., disposed off the center axis), and approximately 9 seconds were taken when the heating member 3 was disposed eccentrically (offset) and brought in contact with the inner wall of the hollow oxygen sensing element 2. Thus, the rise time of the oxygen sensor 1 is remarkably reduced. From these facts, it is seen that even when the exhaust gas temperature is low, e.g., at the start of the automobile engine or at the time of idling, the oxygen sensor 1 properly determines the oxygen concentration at an early stage, to thereby achieve exhaust gas purification with more precise and at higher resolution.

Figure 18:
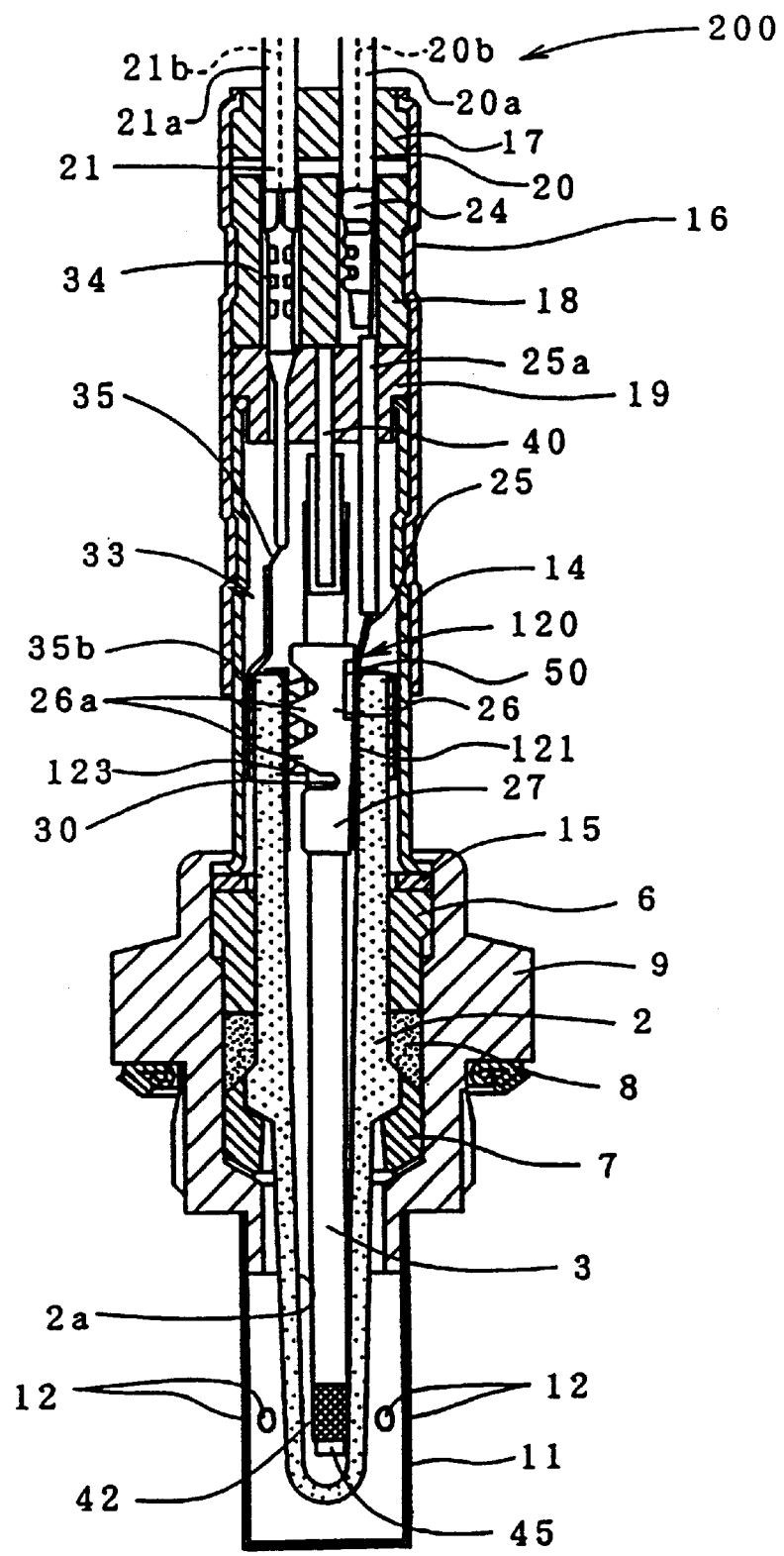
FIG. 18 shows a longitudinal sectional view showing still another modified embodiment of the oxygen sensor shown in FIG. 1.

Modifications of the oxygen sensor 1 according to the embodiment described above will be described next. The same features as those of the embodiment described above are denoted by common reference numerals, and description thereof is omitted. Primarily, any points of difference from the embodiment described above are described. FIG. 18 shows an oxygen sensor 200 which employs an internal electrode connection member 120 and a fixture member 123 in place of the terminal member 23. The internal electrode connection member 120 includes a cylindrical internal electrode connecting portion 121 which is inserted into an open end portion of the hollow oxygen sensing element 2. A rear end portion of the internal electrode connecting portion 121 assumes a structure that combines the connector portion 24 and the lead-out strip portion 25 (covered with the insulating tube 25a) connected to the connector portion 24 as observed in the terminal member 23 of the oxygen sensor 1 shown in FIG. 1.

Figure 19:
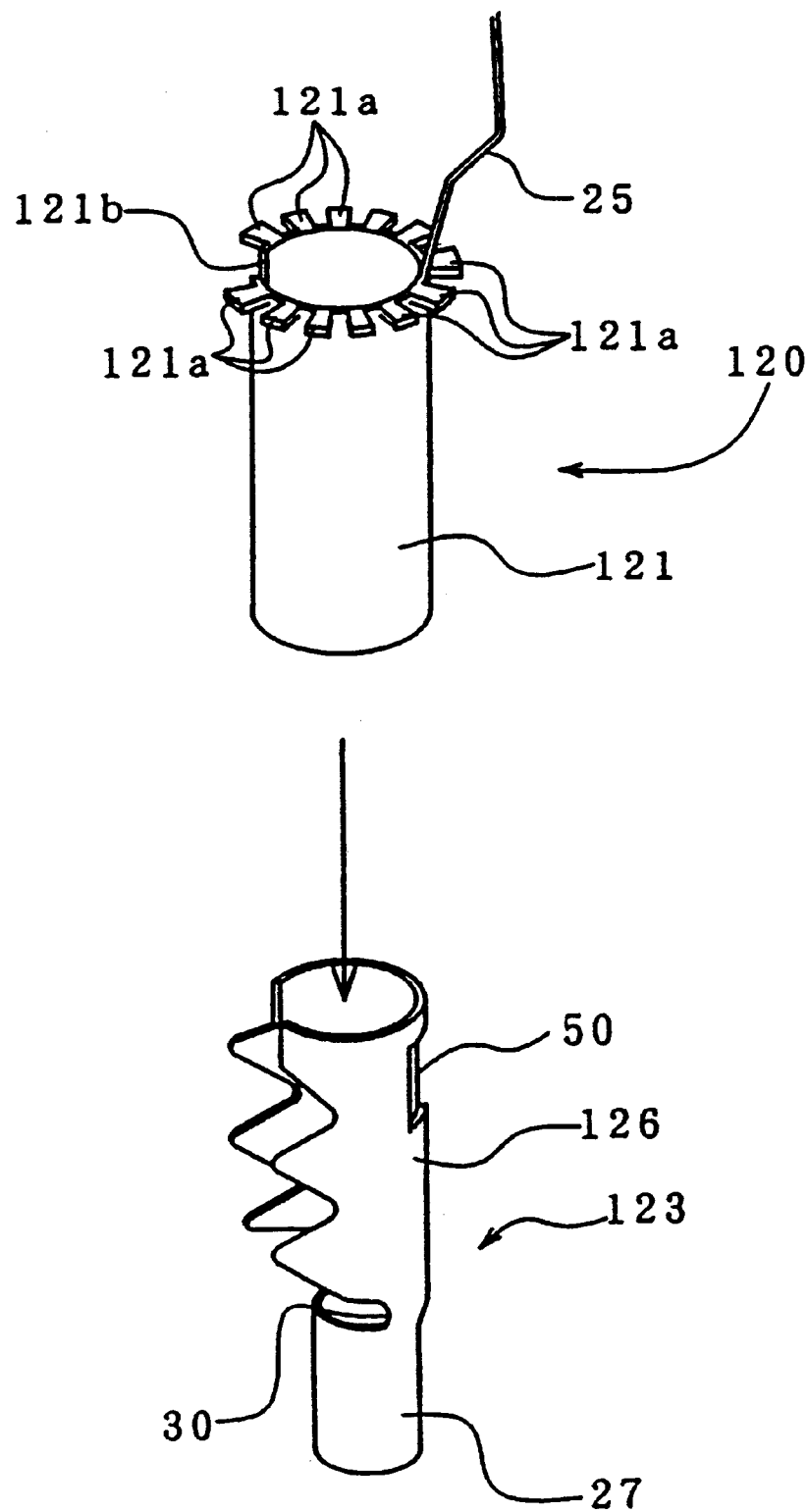
FIG. 19 shows an exploded perspective view of an internal electrode connection member and a fixture member of the oxygen sensor shown in FIG. 18.

As shown in FIG. 19, the internal electrode connecting portion 121 is formed into a substantially cylindrical shape having an axial slit 121b formed therein and a cross section shaped in a letter C. In a free state, the outside diameter of the internal electrode connecting portion 121 is slightly greater than the bore diameter of the open end portion of the oxygen sensing element 2. One end of the lead-out strip portion 25 is integrated with the rear end of the internal electrode connecting portion 121 and positioned opposite the slit 121b. As shown in FIG. 18, when pressed into the oxygen sensing element 2, the internal electrode connecting portion 121 is compressed radially while the slit 121b is contracted. By means of friction induced by an elastically restoring force, the internal electrode connecting portion 121 is fixed on the inner wall of the oxygen sensing element 2. Through contact with the inner electrode layer 2c (FIG. 2) of the oxygen sensing element 2, the internal electrode connecting portion 121 functions to lead an output voltage out from the oxygen sensing element 2 through the lead-out strip portion 25. A plurality of engagement projections 121a project outward from an open rear end edge of the internal electrode connecting portion 121. The engagement projections 121a are engaged with the open end of the hollow portion of the oxygen sensing element 2 to thereby axially position the internal electrode connecting portion 121.

The fixture member 123 assumes a shape substantially equivalent to that of the terminal member 23 of FIG. 1 after the connector portion 24 and the lead-out strip portion 25 are removed therefrom. The heating-member holding portion 27 is adapted to hold the heating member 3. A fixture portion 126 corresponds to the internal electrode connecting portion 26 of the terminal member 23 shown in FIG. 1 and assumes a shape substantially similar to that of the internal electrode connecting portion 26. The fixture member 123 is pressed into the internal electrode connecting portion 121. By means of friction between the outer surface of the fixture member 123 and the inner wall of the internal electrode connecting portion 121, the heating member 3 is axially positioned within the hollow portion of the oxygen sensing element 2. The fixture portion 126 maintains contact with the inner wall of the oxygen sensing element 2 indirectly, i.e., via the internal electrode connecting portion 121.

Figure 8:
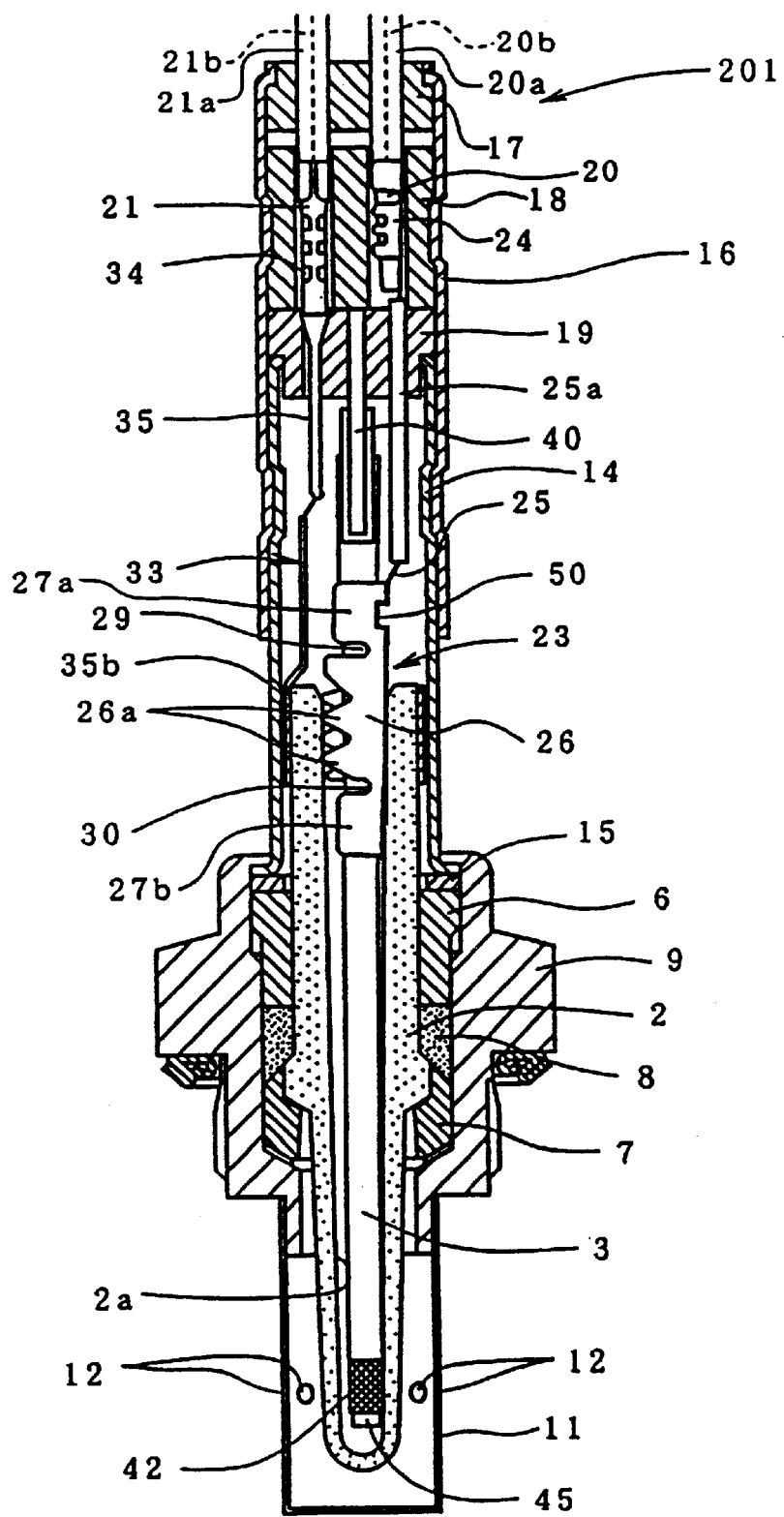
FIG. 8 shows a longitudinal sectional view of a modified embodiment of the oxygen sensor shown in FIG. 1.
Figure 9:
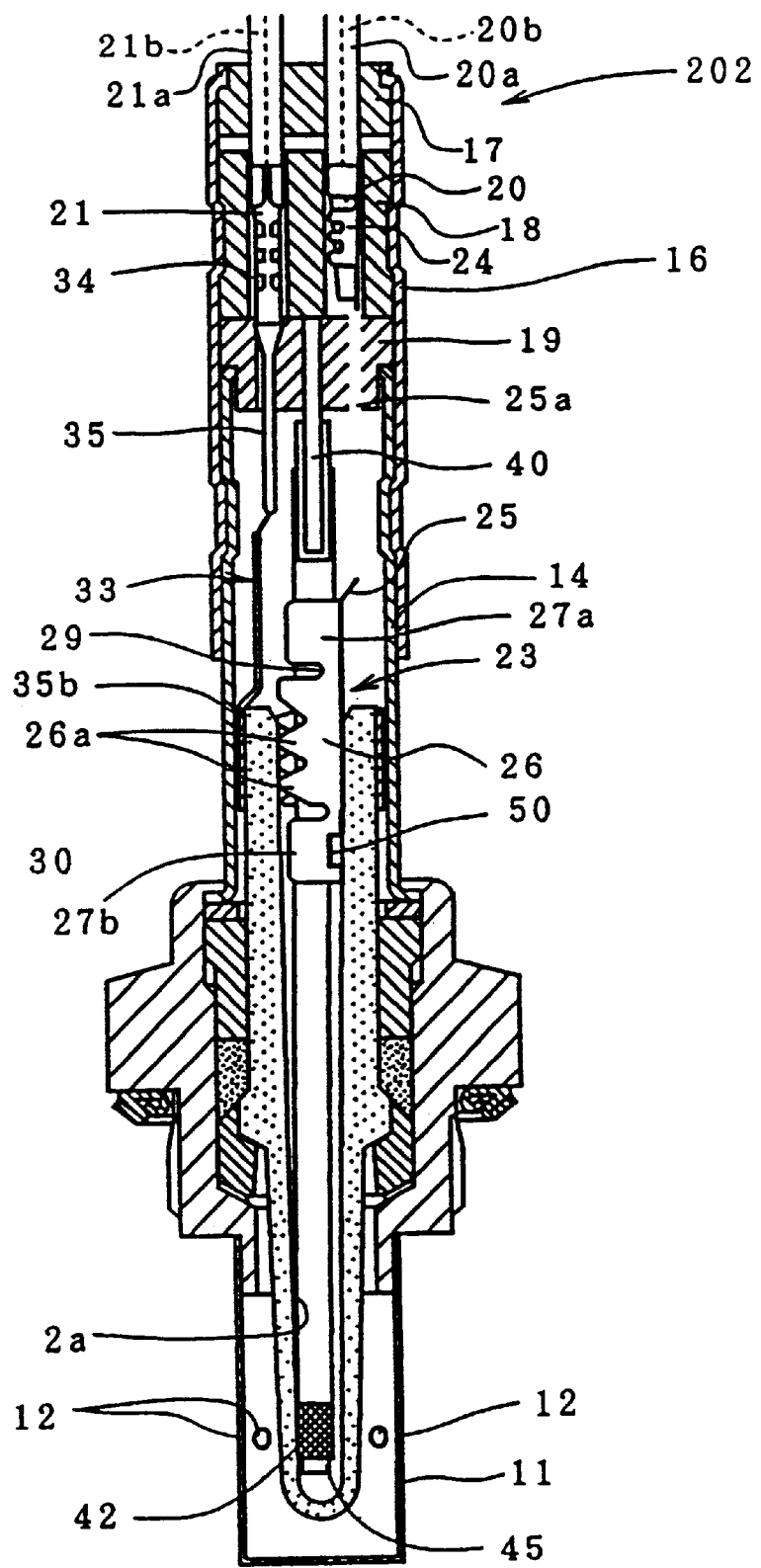
FIG. 9 shows a longitudinal sectional view of another modified embodiment of the oxygen sensor shown in FIG. 1.

As shown in FIGS. 8 and 9, in the terminal member 23, two heating-member holding portions 27a and 27b may be coupled with axially opposite ends of the internal electrode connecting portion 26 via the coupling parts 29 and 30, respectively. The positioning projection 50 may be formed on either the heating-member holding portion 27a or 27b. In this case, the internal diameter of the heating-member holding portion 27a (27b) must be determined in consideration of an inward projection of the positioning projection 50.

Figure 20:
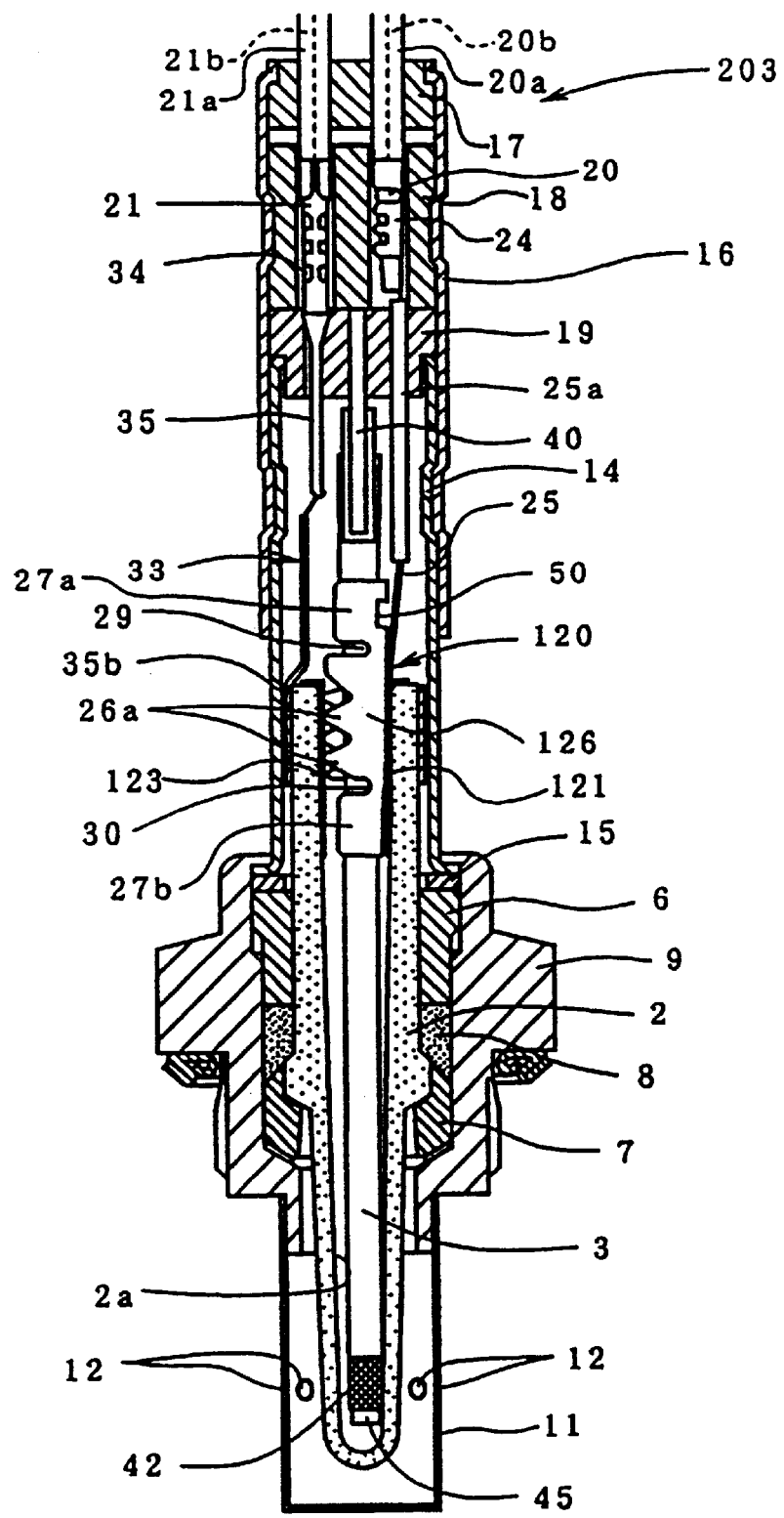
FIG. 20 shows a longitudinal sectional view of a modified embodiment of the oxygen sensor shown in FIG. 8.

In an oxygen sensor 201 shown in FIG. 8, the positioning projection 50 is formed on the heating-member holding portion 27a located on the far side of the internal electrode connecting portion 26 with respect to the heating portion 42. In an oxygen sensor 203 shown in FIG. 20, the terminal member 23 is replaced with the internal electrode connecting portion 120 and the fixture member 123 as in the case of the oxygen sensor 200 shown in FIG. 18.

Figure 21:
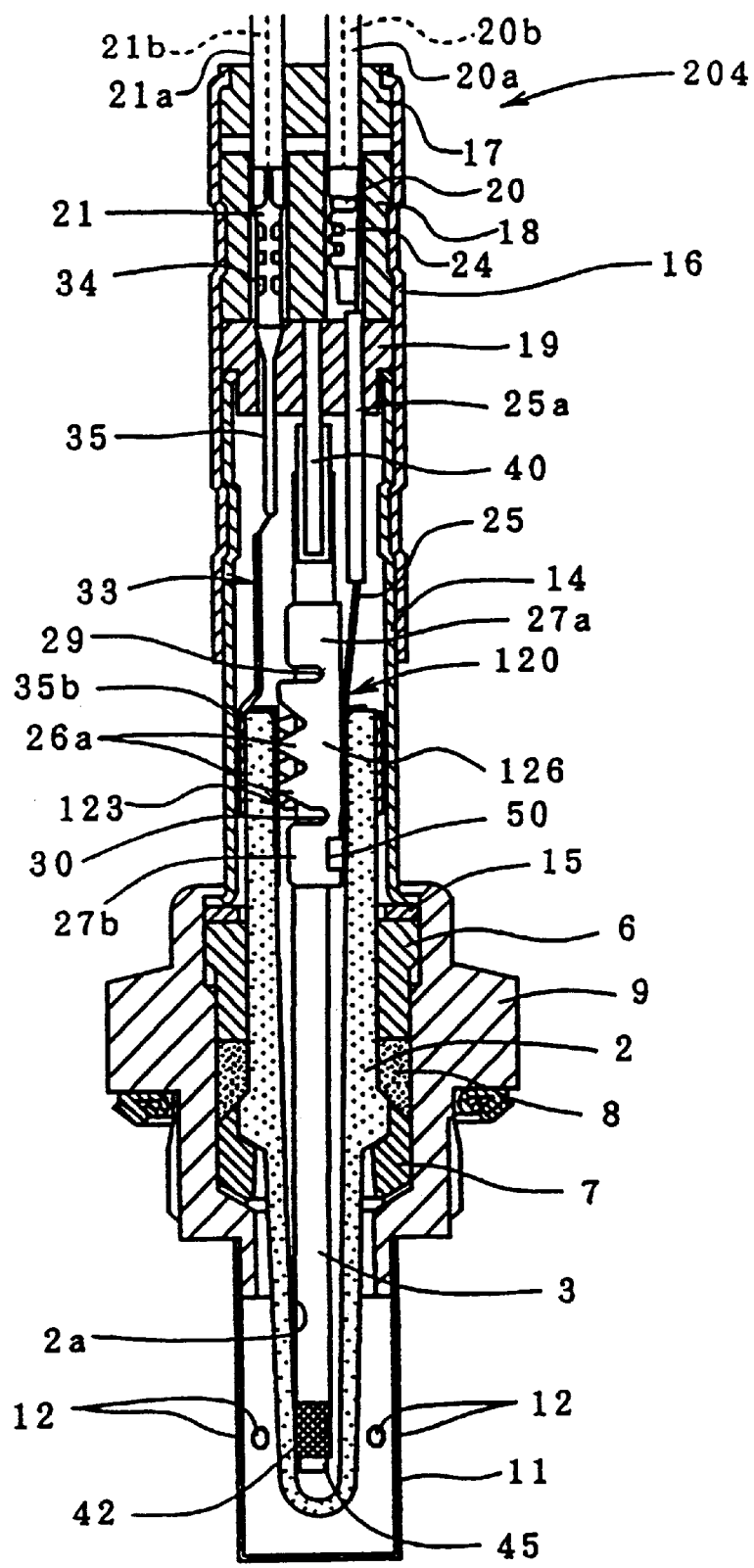
FIG. 21 shows a longitudinal sectional view of a modified embodiment of the oxygen sensor shown in FIG. 9.

In an oxygen sensor 202 of FIG. 9, the positioning projection 50 is formed on the heating-member holding portion 27b located on the near side of the internal electrode connecting portion 26 with respect to the heating portion 42. In an oxygen sensor 204 of FIG. 21, the terminal member 23 is replaced with the internal electrode connecting portion 120 and the fixture member 123. According to the embodiments shown in FIGS. 9 and 21, the heating member 3 abuts a portion of the element inner wall 2a opposite the coupling part 29 or 30. As a result, as shown in FIG. 10, the heating member 3 is inclined with respect to the oxygen sensing element 2 such that the axis O1 thereof and the axis O2 of the hollow portion of the oxygen sensing element 2 are at a predetermined angle, i.e., inclination θ.

Figure 10:
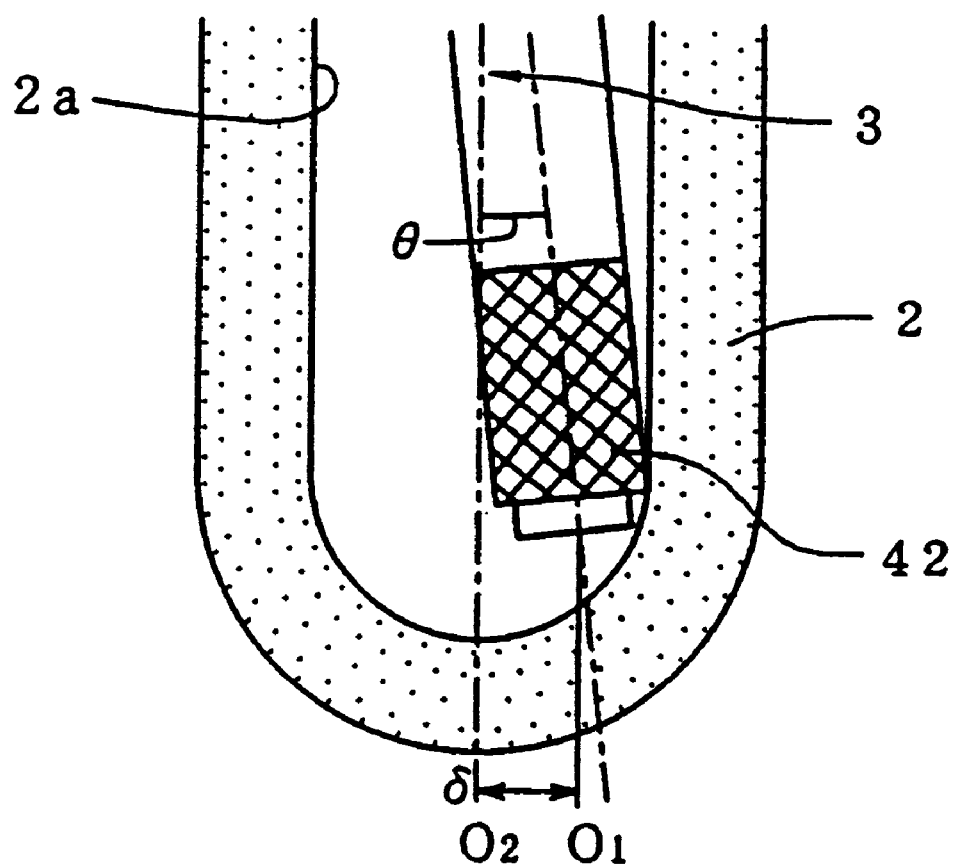
FIG. 10 shows a partial sectional view conceptually illustrating the heating portion shown in FIG. 9 and its neighboring portion.

In FIG. 10, for ease of understanding, the gap between the heating member 3 and the oxygen sensing element 2 and an inclination θ of the heating member 3 in relation to the oxygen sensing element 2 are illustrated in an exaggerated manner. An offset of the axis O1 as measured in the vicinity of the heating portion 42 and with respect to the axis O2 of the oxygen sensing element 2 is represented by. The offset δ and the inclination θ are approximately 0.085 to 0.385 mm and 0.1° to 0.5° when the inside diameter defined by the element inner wall 2a is 2.8 to 3.2 mm and the outside diameter of the heating member 3 is 2.43 to 2.63 mm. This construction permits forming a reliable laterally-abutting structure without giving rise to an excessive pressure between the heating member 3 and the oxygen sensing element 2.

Figure 11:
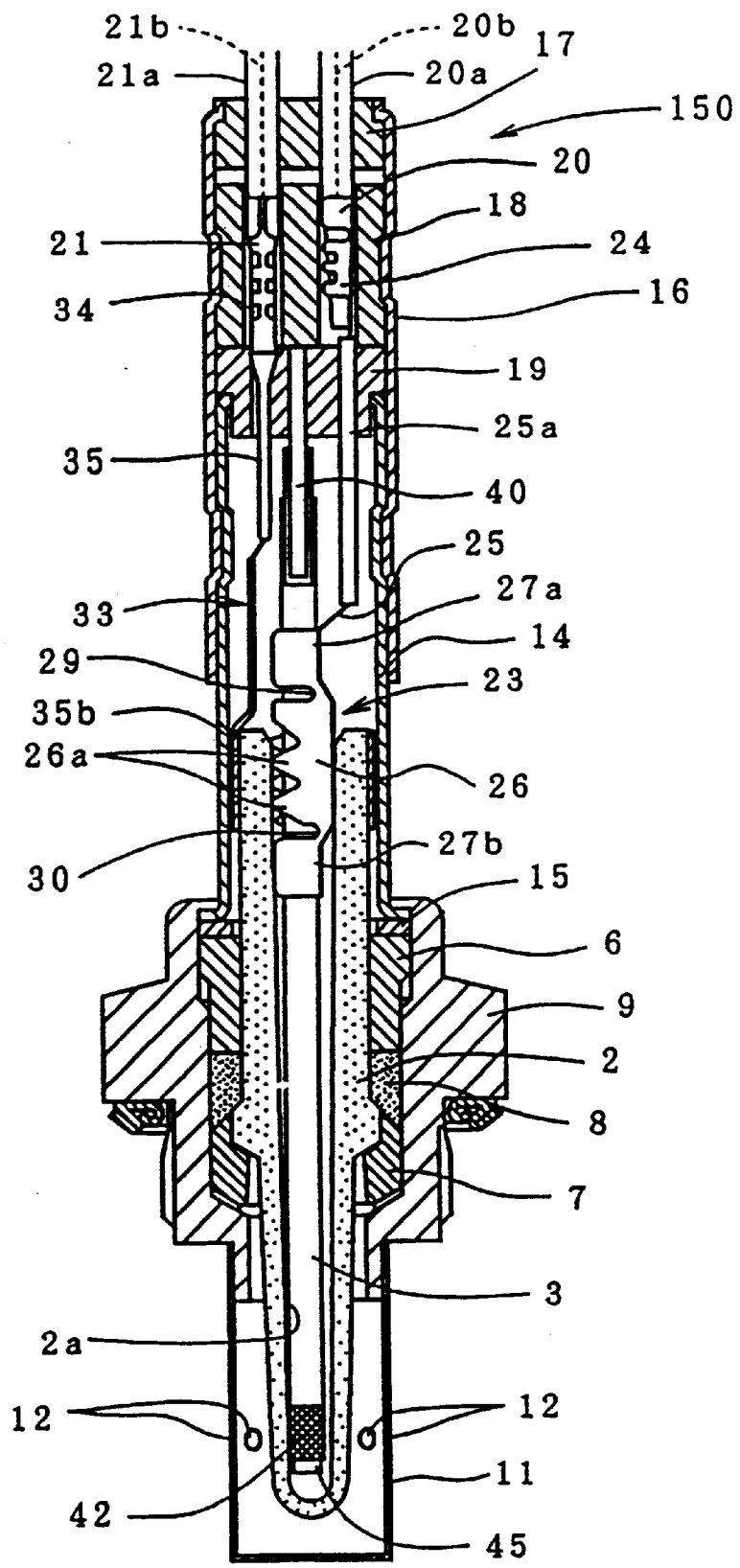
FIG. 11 shows a longitudinal sectional view of an oxygen sensor according to another embodiment of the present invention.

FIG. 11 shows the oxygen sensor according to another embodiment of the present invention. The same structural features as those shown in the embodiment described above are denoted by like reference numerals, and description thereof is omitted. Primarily, points of difference between the previously described embodiment and the present embodiment are described.

Figure 12:
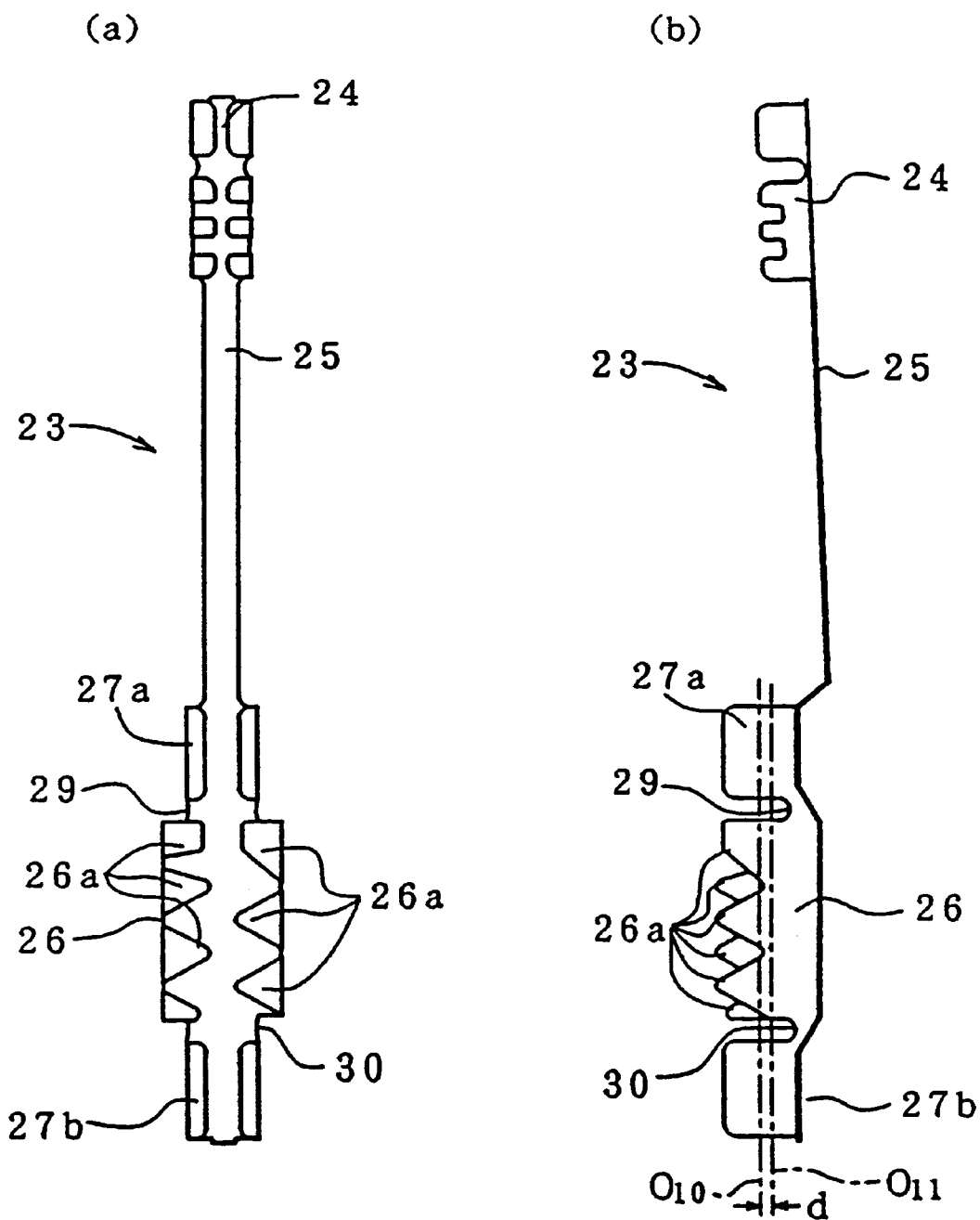
FIGS. 12(a) and 12(b) show the terminal member of FIG. 11 in greater detail.

The structure of the oxygen sensor 150 shown in FIG. 11 is different from that of the oxygen sensor 1 described above in connection with the previous embodiment in the following points. The terminal member 23 includes an internal electrode connecting portion 26 substantially identical to that of the terminal member 23 of the previously described embodiment (FIG. 1). The internal electrode connecting portion 26 is provided with a first heating-member holding portion 27a formed at one end as viewed in the axial direction of the heating member 3 and a second heating-member holding portion 27b formed at the other end. Those first and second heating-member holding portions 27a and 27b each assume construction substantially identical to that of the heating-member holding portion 27 of the previously described embodiment. As shown in FIG. 12, the heating-member holding portions 27a and 27b are coupled with the internal electrode connecting portion 26 such that a common axis O10 thereof is disposed substantially parallel and eccentric to an axis O11 of the hollow portion of the oxygen sensing element 2.

Specifically, in the terminal member 23, the first heating-member holding portion 27a and the second heating-member holding portion 27b are integral with the corresponding opposite ends of the internal electrode connecting portion 26 and are oriented in the same manner with respect to the heating member 3. A first coupling part 29 and a second coupling part 30 intervene between the internal electrode connecting portion 26 and the heating-member holding portions 27a and 27b, respectively. The first coupling part 29 and the second coupling part 30 are stepwise bent inward in the radial direction of the internal electrode connecting portion 26. A degree of the bending is adjusted so as to produce the following eccentricity (offset) between the axis O10 of the heating-member holding portions 27a and 27b and the axis O11 of the hollow portion of the oxygen sensing element 2. The axis O10 is substantially parallel to the axis O11 of the hollow portion and is biased by a predetermined amount d and away from the coupling parts 29 and 30 with respect to the axis O11.

Figure 13:
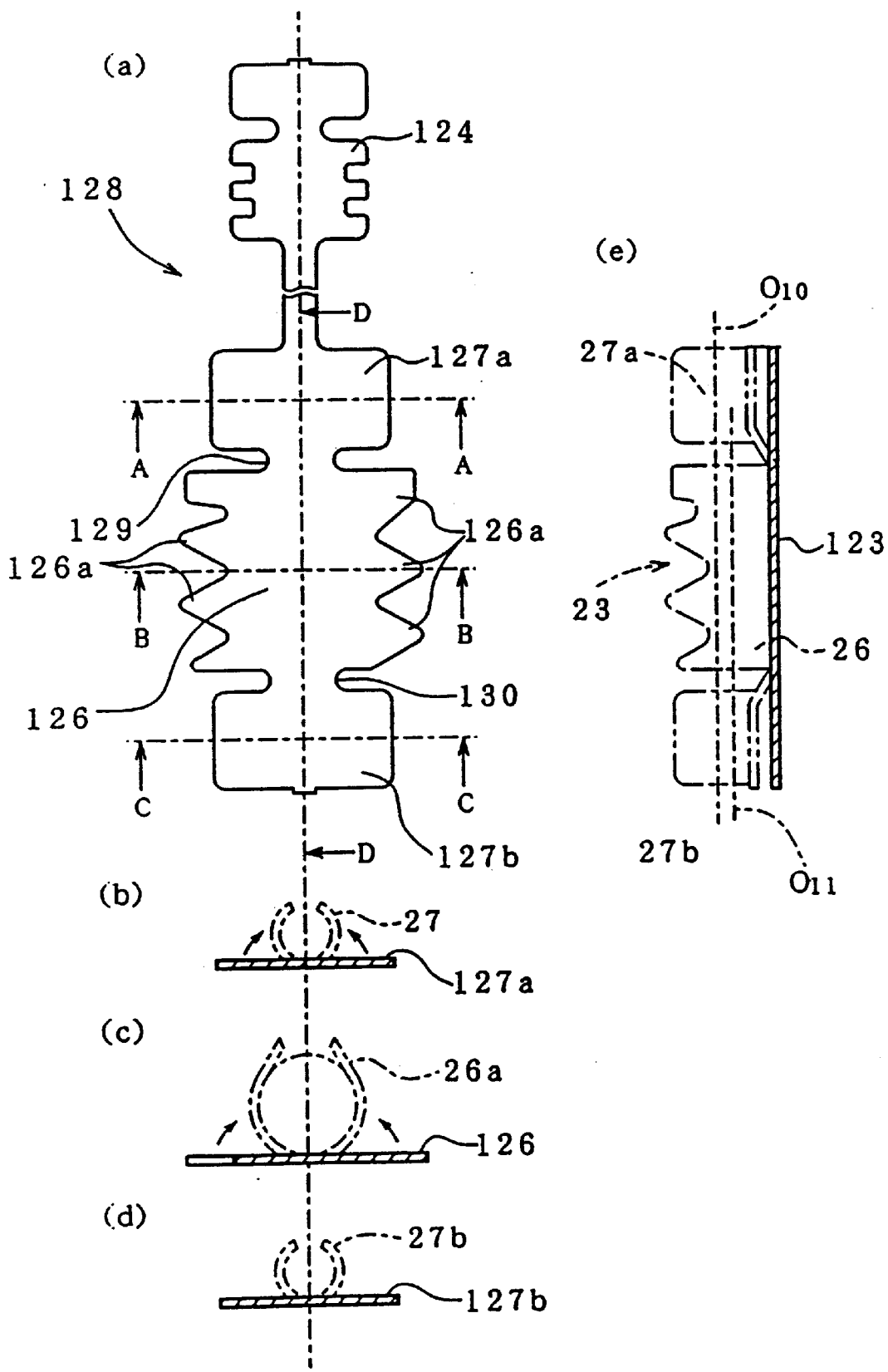
FIGS. 13(a)–(e) show an example of a blank sheet for forming the terminal member shown in FIG. 12.

The terminal member 23 may be manufactured by bending a metal blank sheet 128 configured as shown in FIG. 13. As shown in FIG. 13(a), the metal blank sheet 128 includes three sections 127a, 126, and 127b. A connecting part 129 to be the first coupling part 29 connects the sections 127a and 126, and another connecting part 130 to be the second coupling part 30 connects the sections 126 and 127b. As shown in FIGS. 13(b) to 13(d), the sections 127a, 126, and 127b are curved widthwise into a cylindrical member, thereby forming the first heating-member holding portion 27a, the internal electrode connecting portion 26, and the second heating-member holding portion 27b. The first coupling part 29 and the second coupling part 30, as shown in FIG. 13(e), are stepwise bent so as to produce a predetermined eccentricity between the axis O10 of the heating-member holding portions 27a and 27b and the axis O11 of the hollow portion of the oxygen sensing element 2.

The oxygen sensor 150 so configured also yields effects similar to those of the oxygen sensor 1 described in conjunction with the previous embodiment 1 and further yields the result that the two heating-member holding portions 27a and 27b can more stably hold the heating member 3.

Figure 22:
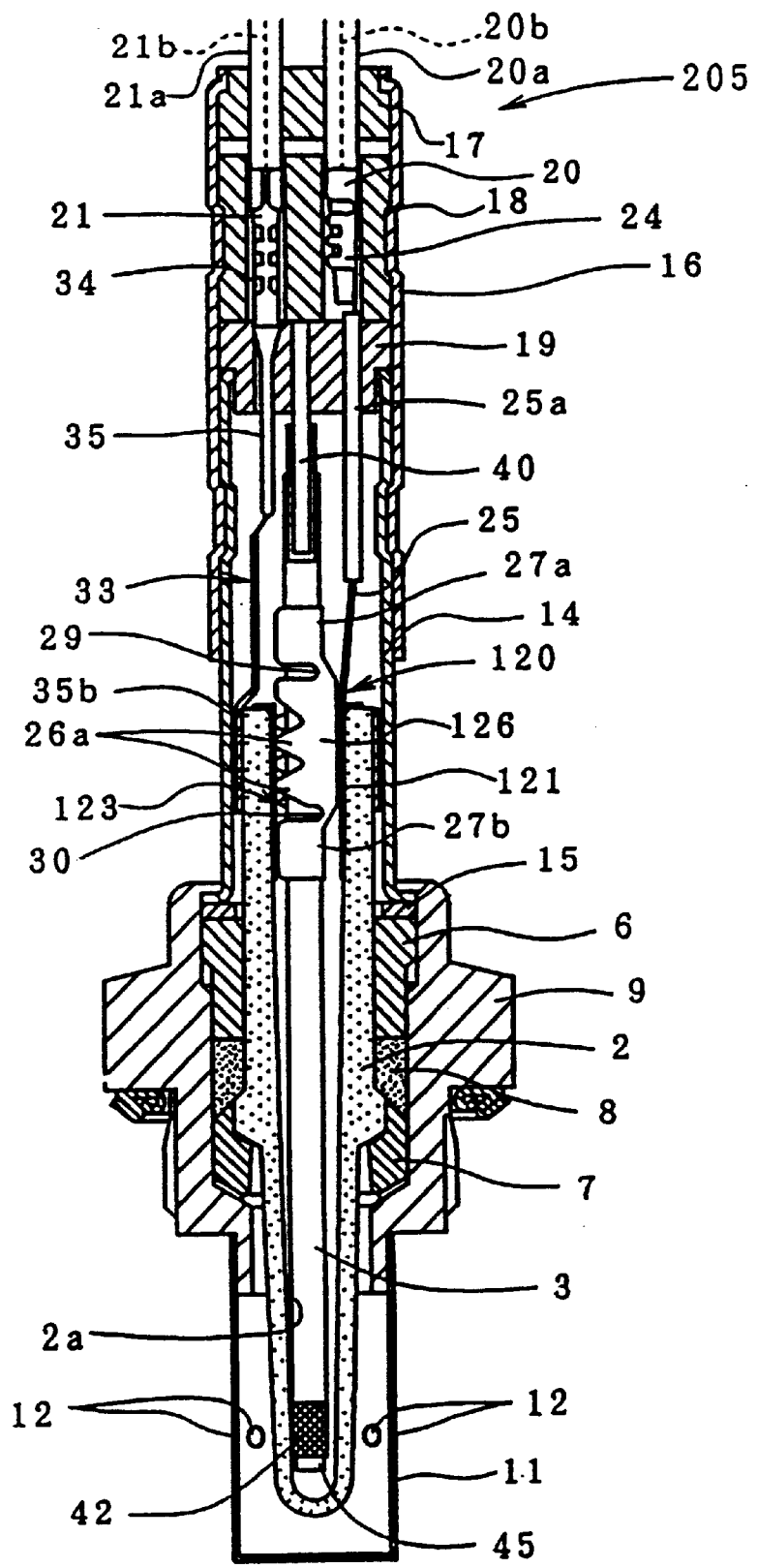
FIG. 22 shows a longitudinal sectional view of a modified embodiment of the oxygen sensor shown in FIG. 11.

FIG. 22 shows an oxygen sensor 205 which is modified from the previous embodiment of the oxygen sensor 150 shown in FIG. 11, in which the terminal member 23 is replaced with an internal electrode connection member 120 and a fixture member 123, as in the case of the oxygen sensor 200 shown in FIG. 18.

Figure 14:
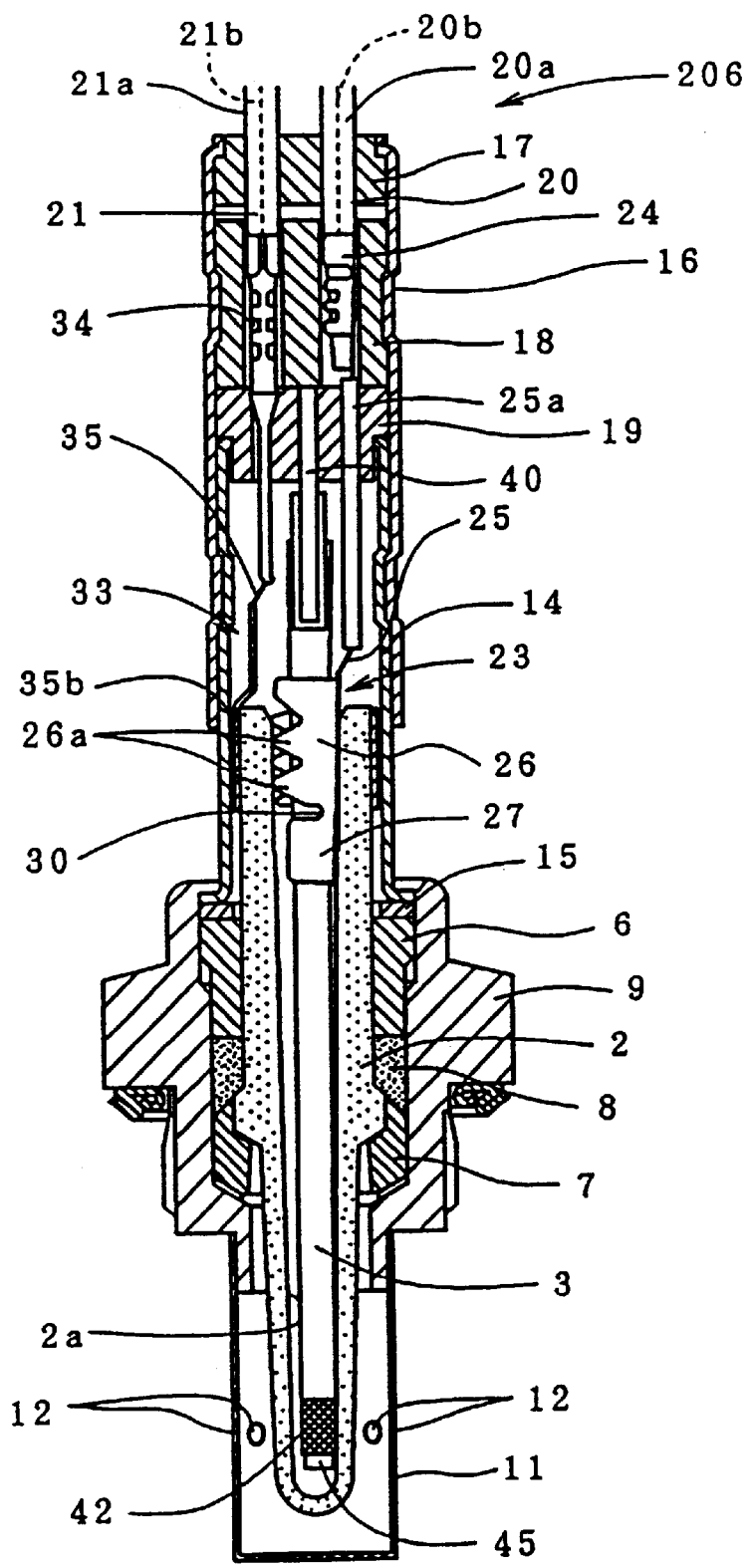
FIG. 14 shows a longitudinal sectional view of a modified embodiment of the oxygen sensor shown in FIG. 11.

In an oxygen sensor 206 of FIG. 14, a heating-member holding portion 27 is coupled with the internal electrode connecting portion 26 only at a near end with respect to the heating portion 42 of the heating member 3, as viewed in the axial direction of the heating member 3. Through employment of a single heating-member holding portion 27, some degree of freedom is imparted to the heating member 3 in terms of movement orthogonal to the axis of the heating member 3 while the heating member 3 is held by the heating-member holding portion 27. When the heating member equipped with the terminal member 23 is inserted into the hollow portion of the oxygen sensing element 2, the heating portion 42 of the heating member 3 maintains contact with the inner wall of the oxygen sensing element 2 and is positioned along the inner wall. This positioning feature yields a significant effect in terms of a reduction in the activation time of the oxygen sensor 206. In this case, through adjustment of ΔD or ΔD/DB to the aforementioned range, the heating portion 42 of the heating member 3 is more readily positioned along the inner wall of the hollow portion of the oxygen sensing element 2. Thus, the activation time of the oxygen sensor is more effectively reduced.

Further, the heating member 3 is less susceptible to an excessive lateral force which might otherwise be applied thereto via the terminal member 23, thereby preventing, for example, potential breakage of the heating member 3 during sensor assembly work. Since the length of the terminal member along the axial direction of the heating member 3 can be reduced, the oxygen sensor 206 is reduced in length along the axial direction of the heating member 3 and hence becomes more compact.

Figure 23:
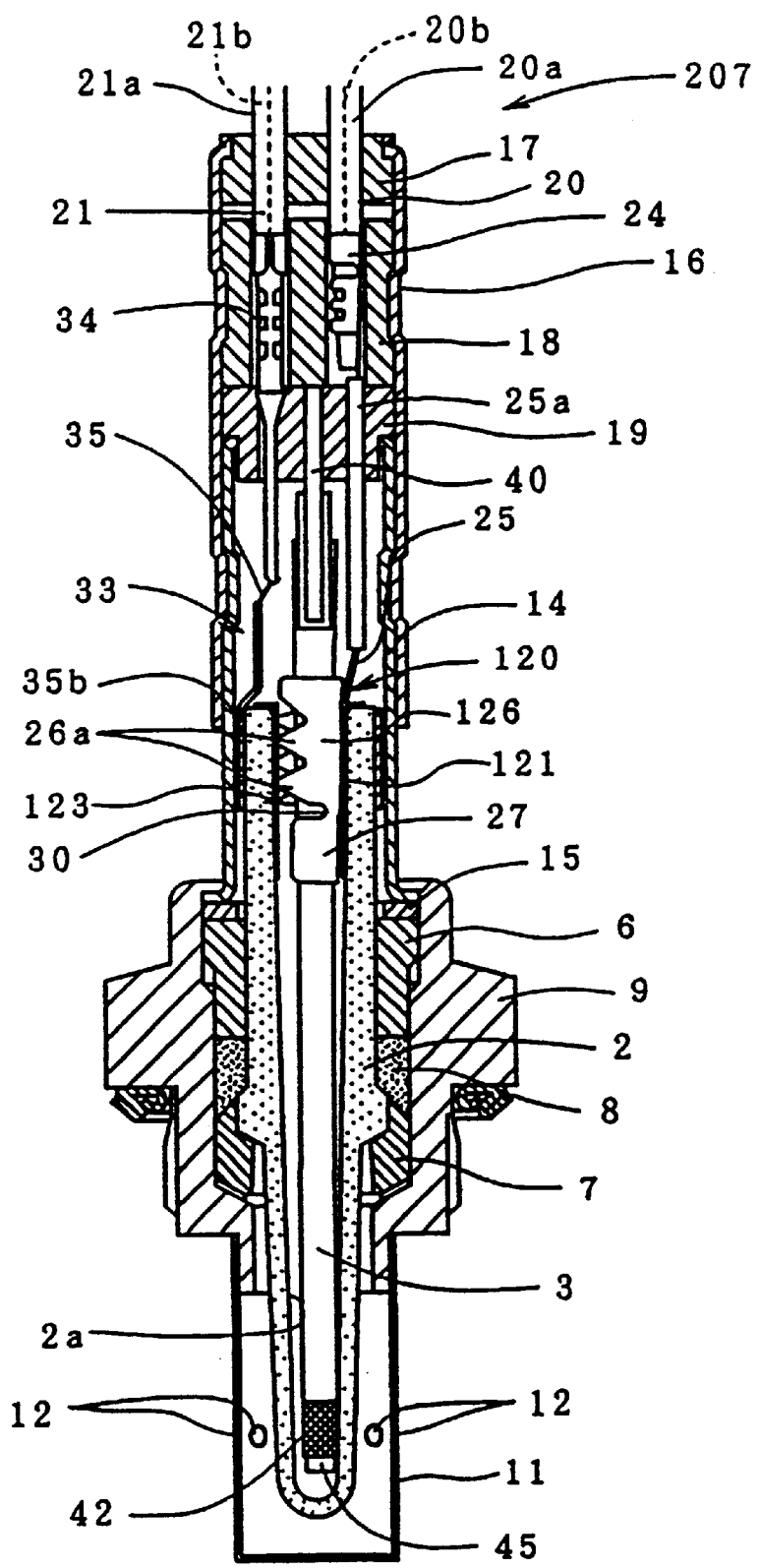
FIG. 23 shows a longitudinal sectional view of a modified embodiment of the oxygen sensor shown in FIG. 14.

FIG. 23 shows an oxygen sensor 207 which is a modification of the previous embodiment of the oxygen sensor 206 shown in FIG. 14, in which the terminal member 23 is replaced with an internal electrode connection member 120 and a fixture member 123, as in the case of the oxygen sensor 200 shown in FIG. 18.

The embodiments of the invention described above are described in greater detail by using the following experimental examples.

EXPERIMENTAL EXAMPLE 1

Six combinations of the inside diameter (average value) DA defined by the tapered inner wall of the hollow oxygen sensing element 2 and the outside diameter DB of the heating member 3, as shown in Table 1, were used. Fifty oxygen sensors 1, as shown in FIG. 1, were manufactured for each combination. The oxygen sensing elements 2 were manufactured as sensing elements from a $ZrO_2$ solid electrolyte, which contains 8.5 to 9.0% $Y_2O_3$ by weight. The $ZrO_2$ solid electrolyte was obtained by the steps of mixing $ZrO_2$ powder with $Y_2O_3$ as a stabilizing agent, molding the resultant mixture, and sintering the resultant molding. The difference ΔD (=DA−DB) and the ratio ΔD/DB for each of those combinations are also shown in Table 1. The heating member 3 was inserted into the hollow portion of the oxygen sensing element 2 to a depth of 47.4 mm. The depth was fixed at this value for the oxygen sensors 1 to be tested. The heating portion 42 had a width of 4 mm as measured in the axial direction of the heating member 3 and an output power of 10 W when a voltage of 12 V is applied thereto.

The oxygen sensing elements 2 of these oxygen sensors 1 underwent a performance test in the following manner. The lead wire 21 (the outer electrode layer 2b) was connected to the positive terminal of a constant DC voltage source (at 4V) through a resistor of 800 kΩ, while the lead wire 20 (the inner electrode layer 2c) was grounded. In this state, a constant voltage of 14 V was applied to the heating portion 42 of the heating member 3 so as to heat the oxygen sensing element 2. A variation of the electrical resistance of each oxygen sensing element 2 was continuously monitored using a divided voltage applied to the oxygen sensing element 2. It was judged that the oxygen sensing element 2 had been activated when the monitored electrical resistance reached 5.6 MΩ. Time that elapsed between start of current application and completion of activation was measured as a sensor rise time for each of the oxygen sensors 1. Table 1 shows average values and standard deviations of the sensor rise time for individual combinations. Variations of the average value Tav and the standard deviation $\sigma_T$ of the sensor rise time with the difference ΔD and the ratio ΔD/DB are plotted in FIGS. 16 and 17.

TABLE 1

| No. | Inside dia. DA of element (mm) | Outside dia. DB of heater (mm) | ΔD = DA − DB (mm) | ΔD/DB | Average value Tav of sensor rise time (sec) | Standard deviation $\sigma_T$ of sensor rise time (sec) |
|---|---|---|---|---|---|---|
| 1 | 2.9 | 2.8 | 0.10 | 0.036 | 6.51 | 0.77 |
| 2 | 2.9 | 2.75 | 0.15 | 0.055 | 6.74 | 0.79 |
| 3 | 3.0 | 2.8 | 0.20 | 0.071 | 6.45 | 0.70 |
| 4 | 3.0 | 2.75 | 0.25 | 0.091 | 7.27 | 0.97 |
| 5 | 3.1 | 2.75 | 0.35 | 0.127 | 7.11 | 0.72 |
| 6 | 3.0 | 2.60 | 0.40 | 0.154 | 6.98 | 1.38 |

Figure 16:
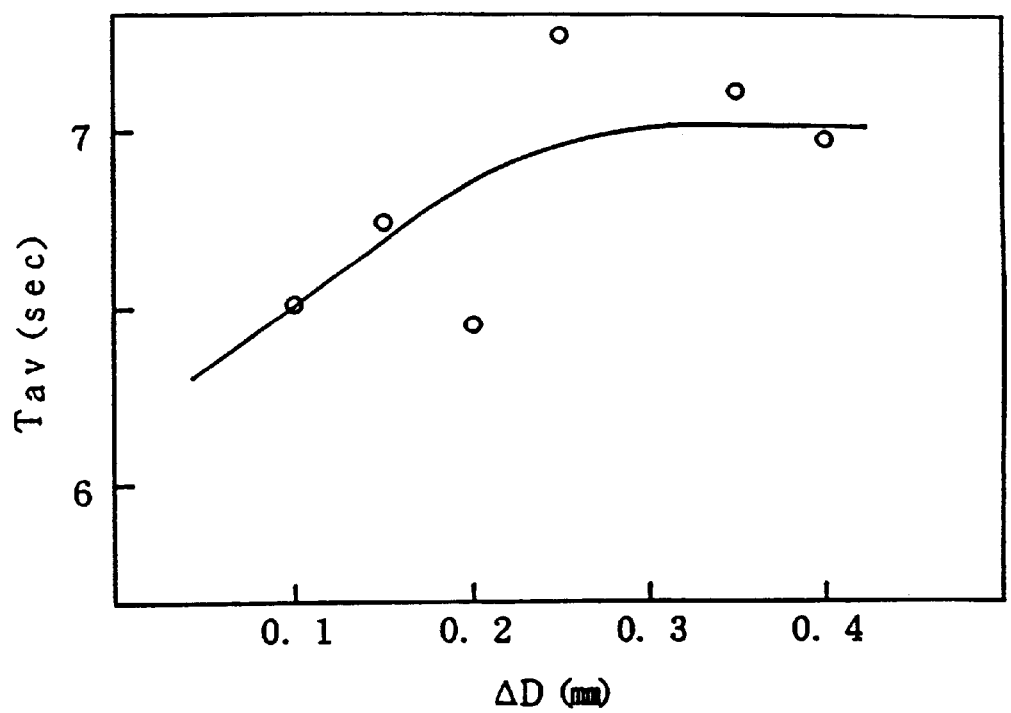
FIGS. 16(a) and 16(b) are graphs showing variations of experimentally obtained Tav and $\sigma_T$ with ΔD.
Figure 16:
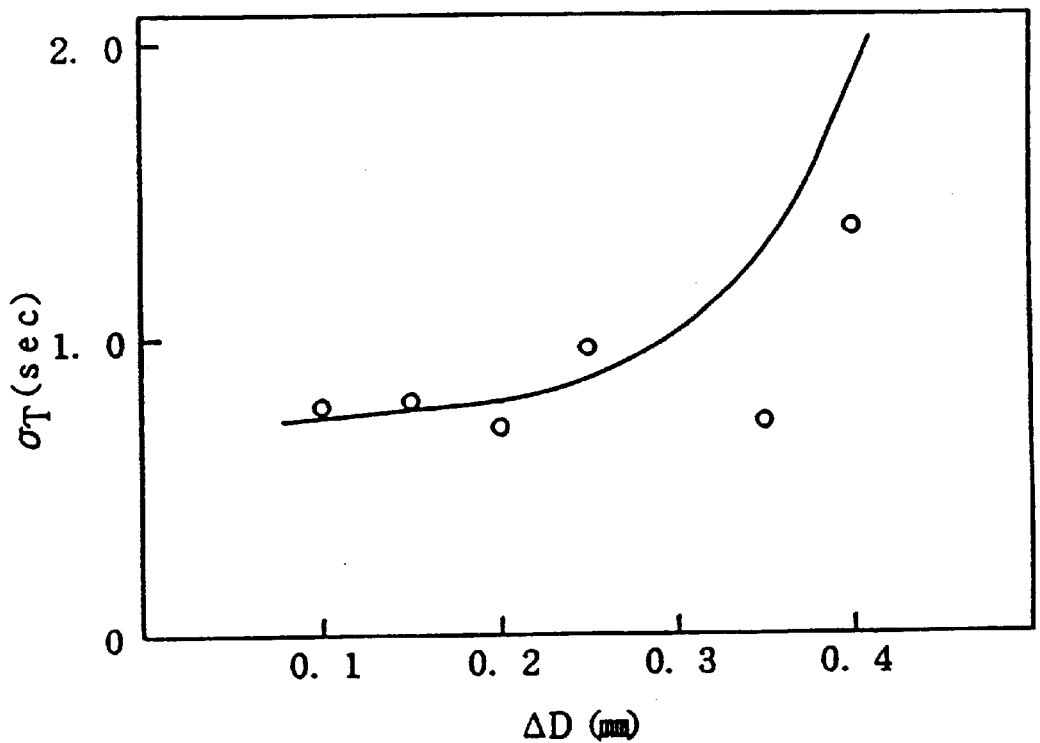
Figure 17:
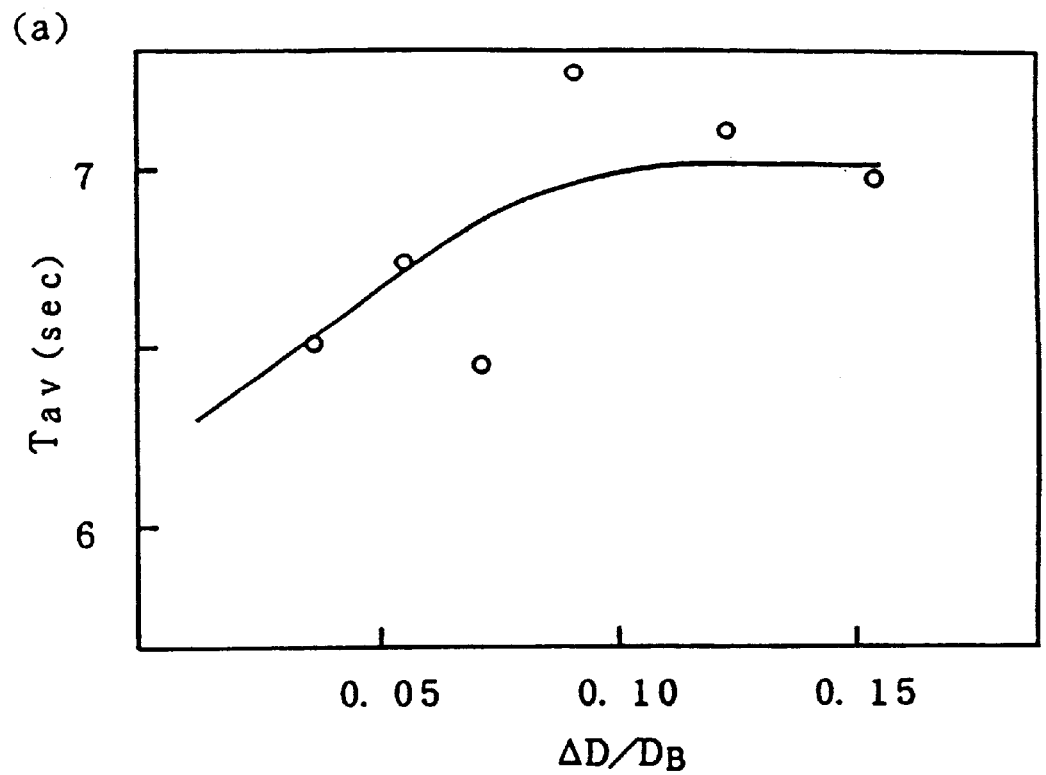
FIGS. 17(a) and 17(b) are graphs showing variations of experimentally obtained Tav and $\sigma_T$ with ΔD/DB.
Figure 17:
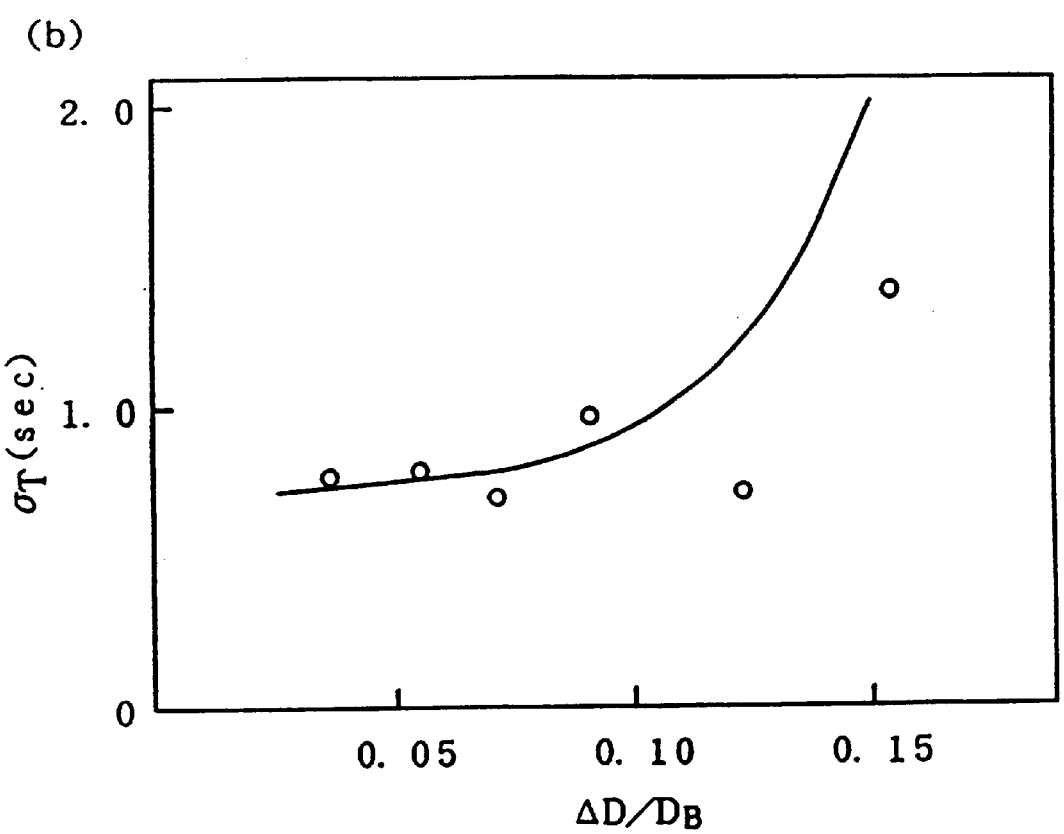

As seen from FIG. 16, the average value Tav of the sensor rise time sharply increases with ΔD. When ΔD exceeds 0.35 mm, the standard deviation $\sigma_T$ of the sensor rise time, or variation of the sensor rise time among the oxygen sensors 1, abruptly increases. To suppress variation of the sensor rise time among individual oxygen sensor products, ΔD is preferably set to not greater than 0.35 mm. As seen from FIG. 17, ΔD/DB is preferably set to not greater than 0.13 (more preferably not greater than 0.10) in terms of suppression of variation of the sensor rise time among individual oxygen sensor products.

EXPERIMENTAL EXAMPLE 2

Six combinations of the inside diameter (average value) DA defined by the tapered inner wall of the hollow oxygen sensing element 2 and the outside diameter DB of the heating member 3 similar to those of experimental example 1 were used. 50 oxygen sensors 150 shown in FIG. 11 were manufactured for each combination. The oxygen sensing element 2 and the heating member 3 similar to those of experimental example 1 were used. The heating member 3 was inserted into the hollow portion of the oxygen sensing element 2 to a depth of 47.4 mm. The depth was fixed at this value for the oxygen sensors 150 to be tested. These oxygen sensors 150 underwent a performance test similar to that of experimental example 1. Table 2 shows average values Tav and standard deviations $\sigma_T$ of the sensor rise time for individual combinations.

TABLE 2

| No. | Inside dia. DA of element (mm) | Outside dia. DB of heater (mm) | ΔD = DA − DB (mm) | ΔD/DB | Average value Tav of sensor rise time (sec) | Standard deviation $\sigma_T$ of sensor rise time (sec) |
|---|---|---|---|---|---|---|
| 11 | 2.9 | 2.8 | 0.10 | 0.036 | 9.004 | 0.7348 |
| 12 | 2.9 | 2.75 | 0.15 | 0.055 | 9.380 | 0.8369 |
| 13 | 3.0 | 2.8 | 0.20 | 0.071 | 9.597 | 0.9059 |
| 14 | 3.0 | 2.75 | 0.25 | 0.091 | 9.619 | 0.9274 |
| 15 | 3.1 | 2.75 | 0.35 | 0.127 | 9.601 | 1.149 |
| 16 | 3.0 | 2.60 | 0.40 | 0.154 | 10.20 | 1.88 |

The average value Tav of the sensor rise time sharply increases with ΔD. When ΔD exceeds 0.35 mm, the standard deviation $\sigma_Y$ of the sensor rise time, or variation of the sensor rise time among the oxygen sensors 150, abruptly increases. To suppress variation of the sensor rise time among individual oxygen sensor products, ΔD is preferably set to not greater than 0.35 mm. ΔD/DB is preferably set to not greater than 0.13 (more preferably not greater than 0.10) in terms of suppression of variation of the sensor rise time among individual oxygen sensor products.

EXPERIMENTAL EXAMPLE 3

Six combinations of the inside diameter (average value) DA defined by the tapered inner wall of the hollow oxygen sensing element 2 and the outside diameter DB of the heating member 3 similar to those of experimental example 1 were used. Fifty oxygen sensors 206, shown in FIG. 14, were manufactured for each combination. The oxygen sensing element 2 and the heating member 3 similar to those of experimental example 1 were used. The heating member 3 was inserted into the hollow portion of the oxygen sensing element 2 to a depth of 47.4 mm. The depth was fixed at this value for the oxygen sensors 206 to be tested. These oxygen sensors 206 underwent a performance test similar to that of experimental example 1. Table 3 shows average values Tav and standard deviations $\sigma_T$ of the sensor rise time for individual combinations.

TABLE 3

| No. | Inside dia. DA of element (mm) | Outside dia. DB of heater (mm) | ΔD = DA − DB (mm) | ΔD/DB | Average value Tav of sensor rise time (sec) | Standard deviation $\sigma_T$ of sensor rise time (sec) |
|---|---|---|---|---|---|---|
| 21 | 2.9 | 2.8 | 0.10 | 0.036 | 6.23 | 0.525 |
| 22 | 2.9 | 2.75 | 0.15 | 0.055 | 6.25 | 0.572 |
| 23 | 3.0 | 2.8 | 0.20 | 0.071 | 6.33 | 0.745 |
| 24 | 3.0 | 2.75 | 0.25 | 0.091 | 6.39 | 0.759 |
| 25 | 3.1 | 2.75 | 0.35 | 0.127 | 6.78 | 1.014 |
| 26 | 3.0 | 2.60 | 0.40 | 0.154 | 6.98 | 1.321 |

The average value Tav of the sensor rise time sharply increases with ΔD. When ΔD exceeds 0.35 mm, the standard deviation $\sigma_T$ of the sensor rise time, or variation of the sensor rise time among the oxygen sensors 206, abruptly increases. To suppress variation of the sensor rise time among individual oxygen sensor products, ΔD is preferably set to not greater than 0.35 mm. ΔD/DB is preferably set to not greater than 0.13 (more preferably not greater than 0.10) in terms of suppression of variation of the sensor rise time among individual oxygen sensor products.

While preferred embodiments of the invention have been described, such description is for illustrative purposes only, and it should be understood that modifications and variations may be made without departing from the spirit and scope of the invention.

What is claimed is:

1. An oxygen sensor comprising:

an oxygen sensing element having a member formed as a hollow shaft with a hollow portion, the hollow portion having a center axis and an end portion, the oxygen sensing element being closed at the end portion and having an inner and an outer side and an inner wall;

electrode layers disposed on the inner and outer sides of the oxygen sensing element;

a heating member formed as a shaft having a heating portion, a peripheral surface and a center axis, the heating member disposed within the hollow portion of the oxygen sensing element, the heating member adapted to heat the oxygen sensing element;

a fixture member having a fixture portion circumferentially surrounding the heating member and maintaining contact with the inner wall of the oxygen sensing element;

a heating-member holding portion being coupled with the fixture portion while being located adjacent the fixture portion when viewed in an axial direction of the heating member, the heating-member-holding portion being adapted to hold the heating member, thereby fixing the heating member within the oxygen sensing element by using the fixture portion; and a positioning projection formed on the fixture portion so as to project inward and abut the peripheral surface of the heating member, the positioning projection adapted to position the heating member such that the center axis of the heating member is offset in relation to the center axis of the hollow portion of the oxygen sensing element in a vicinity of the heating portion of the heating member.

2. The oxygen sensor according to claim 1, wherein the heating member is disposed such that an entirety of the center axis thereof disposed within the hollow portion of said oxygen sensing element is accommodated within any one of four regions into which the hollow portion of said oxygen sensing element is divided by a first imaginary plane including the center axis of the hollow portion and a second imaginary plane including the center axis of the hollow portion and orthogonal to the first imaginary plane.

3. The oxygen sensor according to claim 1, wherein the heating member is disposed within the hollow portion of the oxygen sensing element such that the center axis of the heating member is substantially parallel to the center axis of the hollow portion.

4. The oxygen sensor according to claim 1, wherein the heating-member holding portion is coupled with the fixture portion only on a side closest to the heating portion of the heating member.

5. The oxygen sensor according to claim 4, wherein the positioning projection is disposed on the fixture portion in a vicinity of an end portion opposite that coupled with the heating-member holding portion and is located at a position corresponding to that where the heating-member holding portion is coupled with the fixture portion.

6. The oxygen sensor according to claim 1, wherein the fixture member serves as a terminal member which includes an internal electrode connecting portion in contact with the electrode layer disposed on the inner side of the oxygen sensing element, and the fixture portion serves as the internal electrode connecting portion.

7. The oxygen sensor according to claim 1, wherein the center axis of said heating member is offset with respect to the center axis of the hollow portion of the oxygen sensing element in a vicinity of the heating portion of the heating member such that a surface of the heating portion is in contact with the inner wall of the hollow portion.

8. The oxygen sensor according to claim 1, wherein a difference $\Delta D$ between internal dimension DA of a cross section of the oxygen sensing element and external dimension DB of a cross section of said heating member ($\Delta D = DA - DB$) is not greater than 0.35 mm.

9. The oxygen sensor according to claim 1, wherein

DA is an average inside diameter of the oxygen sensing element;

DB is an outside diameter of the heating member; and $(DA - DB)/DB \leq 0.13$.

* * * * *